(12) United States Patent
Poola

(10) Patent No.: US 10,416,164 B2
(45) Date of Patent: Sep. 17, 2019

(54) METHODS FOR DETERMINING BREAST CANCER RISK

(71) Applicant: SILBIOTECH, INC., Gaithersburg, MD (US)

(72) Inventor: Indira Poola, Gaithersburg, MD (US)

(73) Assignee: SILBIOTECH, INC., Gaithersburg, MD (US)

( * ) Notice: Subject to any disclaimer, the term of this patent is extended or adjusted under 35 U.S.C. 154(b) by 0 days.

(21) Appl. No.: 15/890,847

(22) Filed: Feb. 7, 2018

(65) Prior Publication Data

US 2018/0224458 A1     Aug. 9, 2018

Related U.S. Application Data

(60) Provisional application No. 62/456,533, filed on Feb. 8, 2017.

(51) Int. Cl.
*G01N 33/574* (2006.01)
*C12Q 1/6874* (2018.01)

(52) U.S. Cl.
CPC ..... *G01N 33/57492* (2013.01); *C12Q 1/6874* (2013.01); *G01N 33/57415* (2013.01); *G01N 33/57484* (2013.01); *G01N 33/57488* (2013.01)

(58) Field of Classification Search
None
See application file for complete search history.

(56) References Cited

U.S. PATENT DOCUMENTS

| | | | |
|---|---|---|---|
| 2004/0058345 A1* | 3/2004 | Poola | C07H 21/04 435/6.14 |
| 2005/0095607 A1* | 5/2005 | Erlander | C07K 14/4748 435/6.12 |
| 2007/0254286 A1* | 11/2007 | Poola | C12Q 1/6886 435/6.16 |
| 2008/0108065 A1* | 5/2008 | Poola | C12Q 1/6886 435/6.14 |
| 2013/0196868 A1 | 8/2013 | Lebowitz et al. | |

FOREIGN PATENT DOCUMENTS

| | | | | |
|---|---|---|---|---|
| WO | WO 2001/058956 | | 8/2004 | |
| WO | WO 2010/003771 A1 | | 1/2010 | |
| WO | WO2013160491 | * | 10/2013 | ........... G01N 33/576 |

OTHER PUBLICATIONS

Poola et al., Molecular risk assessment for breast cancer development in patients with ductal hyperplasias. Clin. Cancer Res. 14, 1274-1280, 2008. (Year: 2008).*
Poola et al., Expression of Carcinoembryonic Antigen Cell Adhesion Molecule 6 oncoprotein in atypical ductal hyperplastic tissues is associated with the development of invasive breast cancer. Clin. Cancer Res. 12, 4773-4783, 2006. (Year: 2006).*
Poola et al., Identification of MMP-1 as a putative breast cancer predictive marker by global gene expression analysis. Nature Medicine, 11, 481-483, 2005. (Year: 2005).*
Poola et al., Molecular constitution of breast but not other reproductive tissues is rich in growth promoting molecules: A possible link to highest incidence of tumor growths. FEBS Letters, 583, 3069-3075, 2009. (Year: 2009).*
Liu et al., Identification of mRNAs differentially-expressed between benign and malignant breast tumour cells. Brit. J. Cancer, 87, 423-431, 2002. (Year: 2002).*
Wyatt et al. Short hairpin RNA—mediated inhibition of matrix Metalloproteinase-1 in MDA-231 cells: Effects on matrix destruction and tumor growth. Cancer Res. 65, 11101-11108, 2005. (Year: 2005).*
Tan et al., HYAL1 overexpression is correlated with the malignant behavior of human breast cancer. Int. J. Cancer, 128, 1303-1315, 2011. (Year: 2011).*
Tsang et al., Expression and clinical significance of carcinoembryonic antigen related cell adhesion molecule 6 in breast cancers. Breast Ca. Res. Treat., 142, 311-322, 2013. (Year: 2013).*
Balk-Møller et al., A marker of endocrine receptor-positive cells, CEACAM6, is shared by two major classes of breast cancer. Luminal and HER2-Enriched. Am. J. Pathol., 184, 1198-1208, 2014. (Year: 2014).*
Lee et al., CEACAM6 as detected by the AP11 antibody is a marker notable for mucin-producing adenocarcinomas. Virchows Arch. 466, 151-159, 2015. (Year: 2015).*
Allred, D. C. et al., "Histological and biological evolution of human premalignant breast disease." Endocr Relat Cancer. Mar. 2001;8(1):47-61.
Black, M.M. et al., "Association of atypical characteristics of benign breast lesions with subsequent risk of breast cancer." Cancer. 29: 338-43 (1972).
Coopey et al., "The role of chemoprevention in modifying the risk of breast cancer in women with atypical breast lesions." Breast Cancer Res. And Treatment, 136(3):627-33(2012).
Dupont, W. D. et al., "Breast cancer risk associated with proliferative breast disease and atypical hyperplasia." Cancer, Feb. 15, 1993;71(4):1258-65.
Dupont, W. D. et al., "Risk factors for breast cancer in women with proliferative breast disease." N. Engl. J. Med. Jan. 17, 1985;312(3):146-51.

(Continued)

*Primary Examiner* — Elly-Gerald Stoica
(74) *Attorney, Agent, or Firm* — Casimir Jones, S.C.; Peter J. Schlueter

(57) ABSTRACT

The present disclosure relates generally to determining the risk of developing breast cancer. In particular, the present disclosure provides materials and methods for determining whether a subject diagnosed with a non-cancerous breast tumor will develop cancer based on expression of multiple oncogenic biomarkers in the non-cancerous breast tumor. The present disclosure also provides a cancer risk score to determine whether a subject has low risk, intermediate risk, or high risk of developing cancer, thereby permitting selection of appropriate therapies to treat the subject. The present disclosure addresses the need for improved diagnostic assessment of early hyperplastic lesions, the presence of which in a subject is a significant indicator that a subject will eventually develop invasive breast cancer.

22 Claims, 17 Drawing Sheets

(56) References Cited

OTHER PUBLICATIONS

Foote, F. W. et al., "Comparative Studies of Cancerous Versus Noncancerous Breasts." Annals of Surgery, Feb. 1945;121(2):197-222.

Guray M. and Sahin A.A., "Benign breast diseases: classification, diagnosis, and management." Oncologist, May 2006;11(5):435-49.

Hartman et al., "Benign breast disease and the risk of breast cancer." New England J. Med, Jul. 21, 2005;353(3):229-37.

Krishnamurthy, et al., "Molecular and biologic markers of premalignant lesions of human breast." Advances in Anatomic Pathology, May 2002;9(3):185-97.

London, S. J. et al., "A prospective study of benign breast disease and the risk of breast cancer." JAMA, Feb. 19, 1992;267(7):941-4.

Page D.L. and Dupont W.D., "Anatomic indicators (histologic and cytologic) of increased breast cancer risk." Breast Cancer Research and Treatment, Nov. 1993;28(2):157-66.

Siegal, et al., "Cancer Statistics" CA: A Cancer Journal for Clinicians, 2017, 67: 7-30.

Karpus et al. "Relationship of fibrocystic disease to carcinoma of the breast." Ann. Surg. 1995;162:1-8.

Tavassoli, F. A and Norris, H.J., "A comparison of the results of long-term follow-up for atypical intraductal hyperplasia and intraductal hyperplasia of the breast." Cancer,Feb. 1, 1990;65(3):518-29.

Wellings et al., "An atlas of subgross pathology of the human breast with special reference to possible precancerous lesions." J. Natl. Cancer Inst. Aug. 1975;55(2):231-73.

Worsham et al., "Breast cancer incidence in a cohort of women with benign breast disease from a multiethnic, primary health care population." Breast J., Mar.-Apr. 2007;13(2):115-21.

Wu et al., "Simultaneous targeting of multiple disease mediators by a dual-variable-domain immunoglobulin." Nature Biotechnology, Nov. 2007;25(11):1290-7.

"BBDRisk DX TM Test Results Report", Silbiotech Inc., Jul. 21, 2017.

\* cited by examiner

Figure 1. Stages of breast cancer progression

FIG. 11A
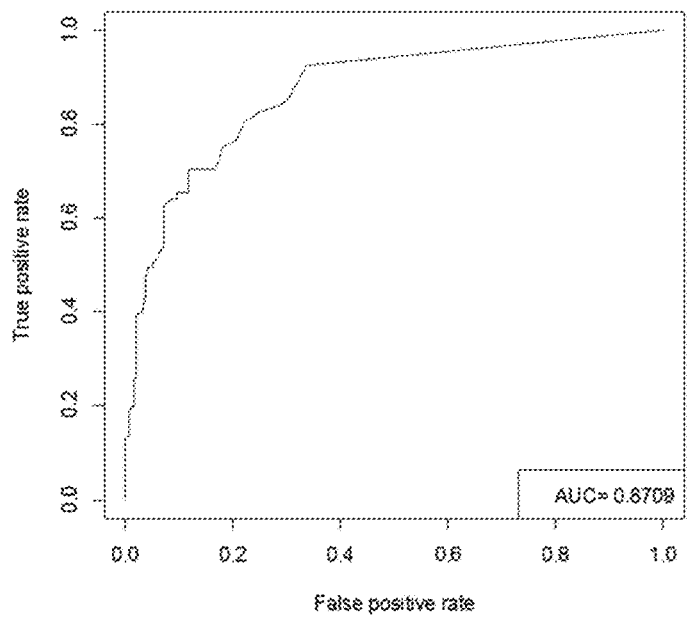
FIG. 11B
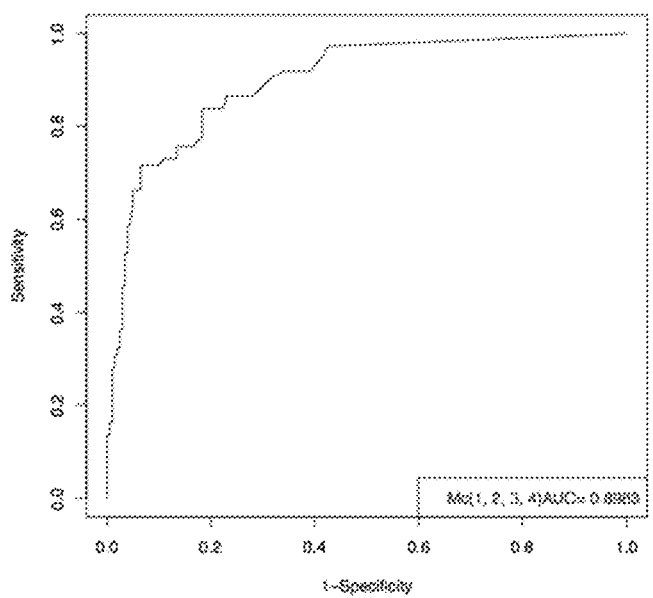
FIGS. 11A-11B

FIG. 12A
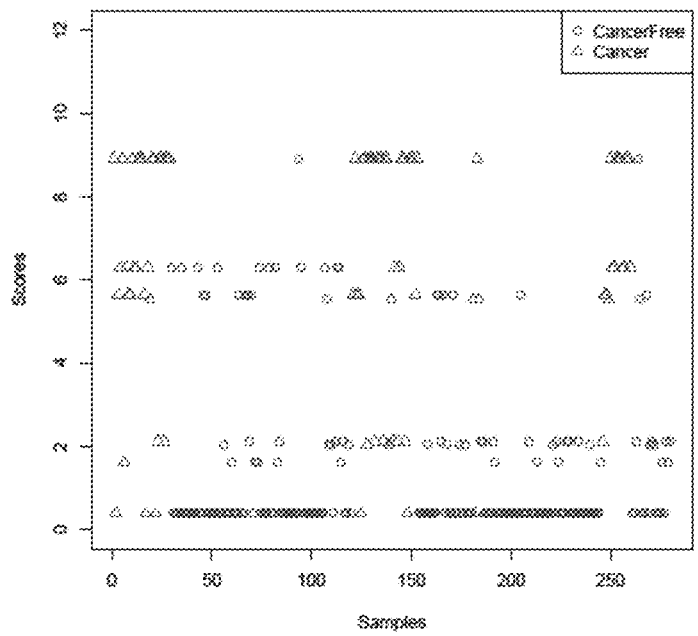
FIG. 12B
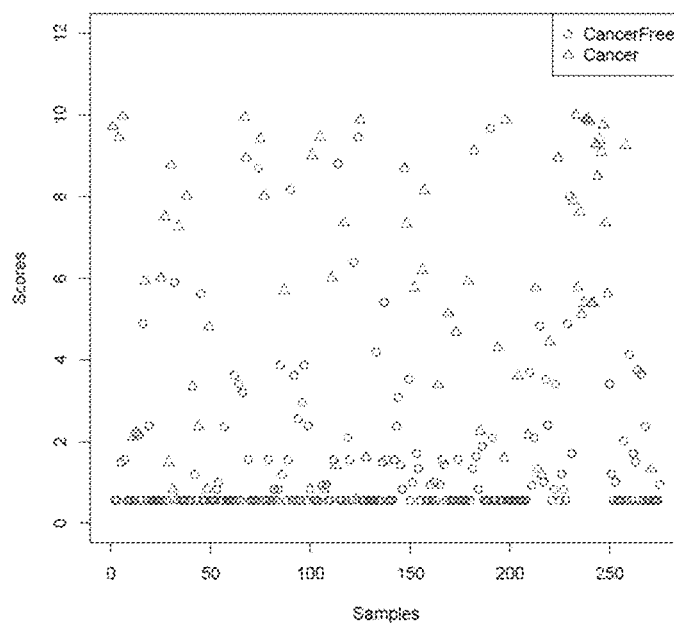
FIGS. 12A-12B

FIG. 13A
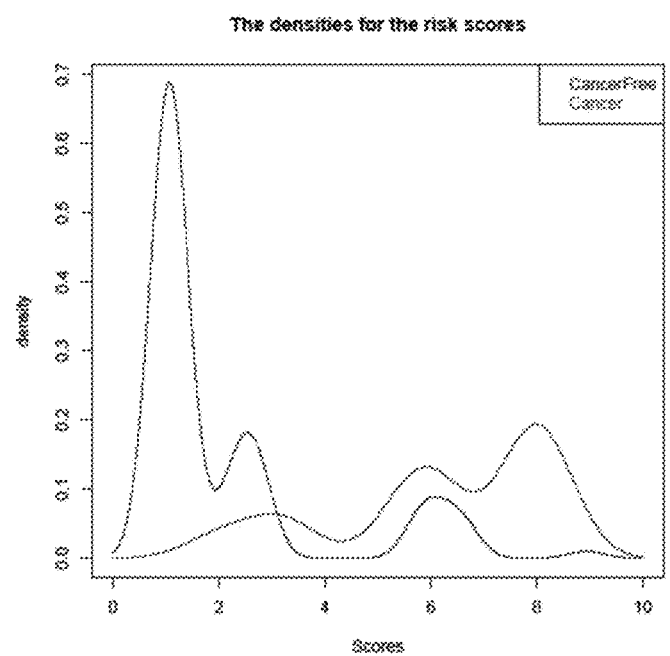
FIG. 13B
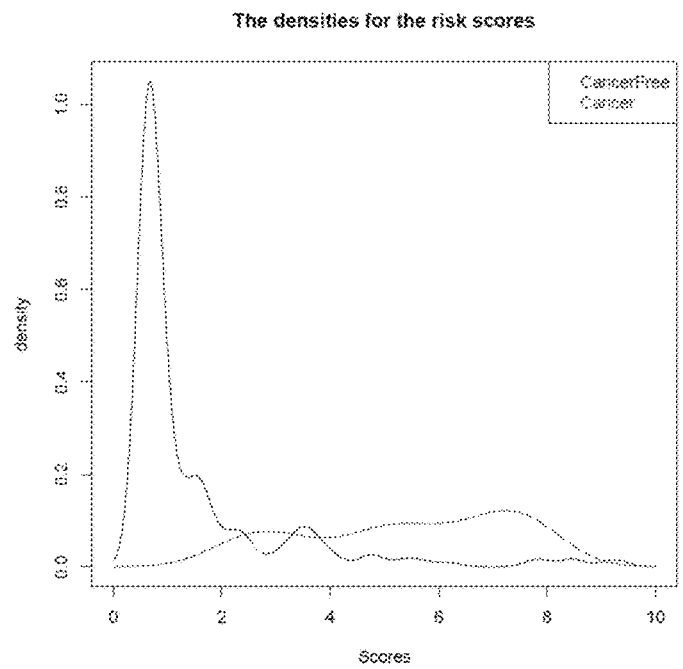
FIGS. 13A-13B

FIG. 14A
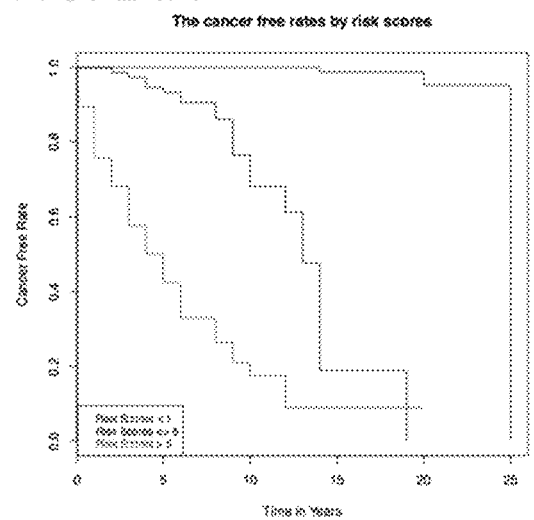
FIG. 14B
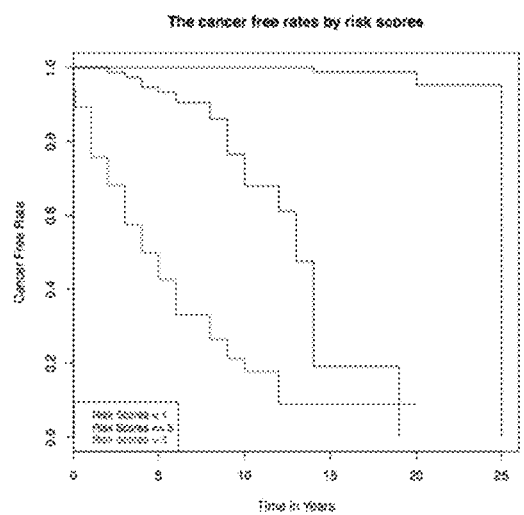
FIG. 14C
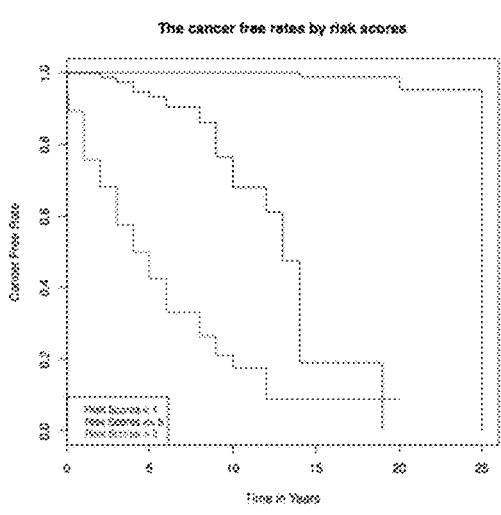
FIGS. 14A-14C

FIG. 17A
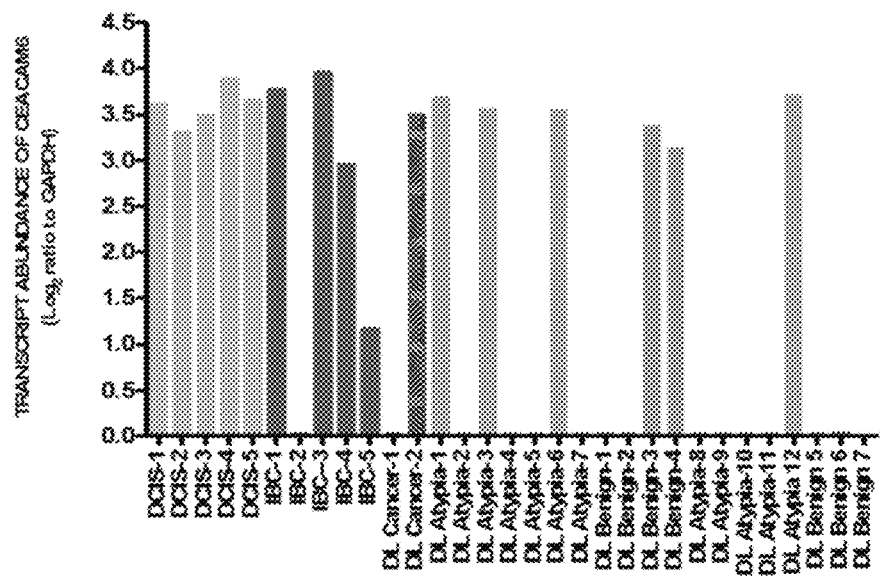
FIG. 17B
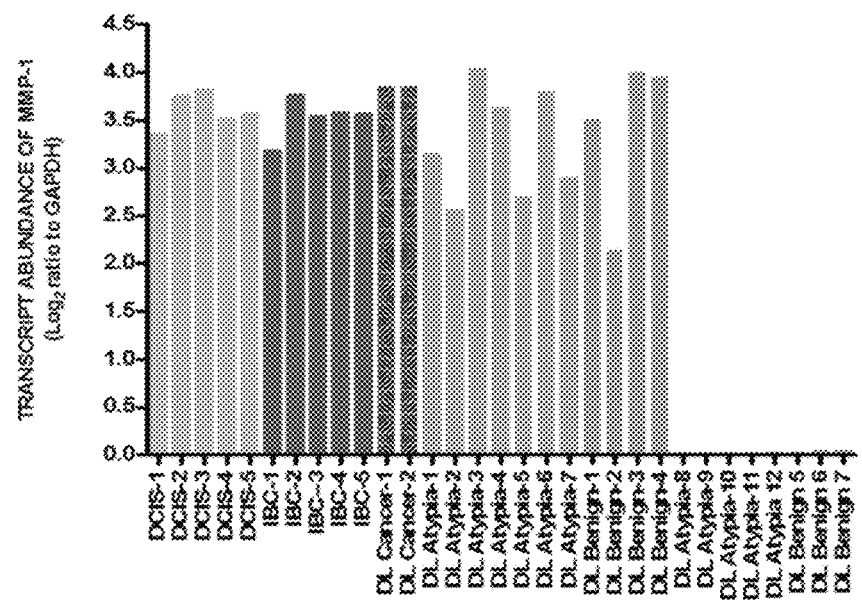
FIGS. 17A-17B

METHODS FOR DETERMINING BREAST CANCER RISK

CROSS-REFERENCE TO RELATED APPLICATION(S)

This application claims priority to and the benefit of U.S. Provisional Patent Application No. 62/456,533, filed on Feb. 8, 2017. This application is incorporated herein by reference in its entirety for all purposes.

GOVERNMENT SUPPORT

The subject matter of this invention was made in part with United States government support under the terms of the following grants: Grant No. IIP-1314287, awarded by the National Science Foundation (NSF); and Grant No. R44CA206774, awarded by the National Cancer Institute at the National Institutes of Health (NIH). The United States government has certain rights in this invention.

FIELD

The present disclosure relates generally to determining the risk of developing breast cancer. In particular, the present disclosure provides materials and methods for determining whether a subject diagnosed with a non-cancerous breast tumor will develop cancer based on expression of multiple oncogenic biomarkers in the non-cancerous breast tumor. The present disclosure also provides a cancer risk score to determine whether a subject has low risk, intermediate risk, or high risk of developing cancer, thereby permitting selection of appropriate therapies to treat the subject.

BACKGROUND

Invasive breast cancer (IBC) is the most diagnosed cancer and the second leading cause of cancer deaths for women in the United States. It is predicted that in the year 2018, about 225,000 women will be diagnosed with IBC and about 40,000 will die from breast cancer (Siegal, et al., A, Cancer Statistics, CA Cancer J. Clin. 68:7-30). Although the mortality rate for breast cancer patients has slightly declined in recent years, it remains very high, mainly due to limited success in curing the cancer after it develops. One rationale for decreasing the mortality rate for breast cancer patients is to identify and treat those patients with high risk developing breast cancer. One cohort recognized to have increased risk for developing breast cancer includes subjects who develop precancerous breast tumors, such as proliferative atypical and non-atypical hyperplasias. For this reason, it would be advantageous to understand the biology of precancerous tumors that have the potential to develop into IBC so that the subjects with precancerous breast tumors at elevated risk can be effectively treated to prevent breast cancer development.

Previous studies have indicated that development of IBC is a multi-step process. Based on animal experiments and epidemiological evidence from humans, it has been proposed that stem cells in terminal duct lobular units undergo proliferation to hyperplasia without atypia, which progress to atypical hyperplasia, then to carcinoma in situ and eventually to IBC (Allred, D. C. et al., Endocrine-Related Cancer, 8:47-61 (2001); Krishnamurthy, et al., Advances in Anatomic Pathology, 9:185-197 (2002)). Several retrospective and prospective studies involving breast biopsies and mastectomy specimens have provided indirect evidence that hyperplastic ducts with and without atypia occur more often in the cancerous breasts than non-cancerous breasts which suggested that hyperplasias are precancerous lesions (Ryan, J. A. et al., Cancer J. Surge, 5:2-8 (1962); Karpus C. M. et al., Ann. Surg, 162:1-8 (1995)). Some retrospective and prospective clinical studies have also established that among the subjects diagnosed with non-cancerous breast tumors, those diagnosed with either atypical hyperplasias or non-atypical hyperplasias have higher risk of developing breast cancer. The relative increased risk of developing breast cancer in a woman with atypical ductal hyperplasia was approximately 5.3 times higher and the risk is two-fold higher for women with non-atypical hyperplasias than those who did not have the above types of tumor growths (Black, M. M. et al., Cancer. 29:338-43 (1972); Dupont, W. D. et al., N. Engl. J. Med. 312:146-51 (1985); Dupont, W. D. et al., Cancer, 71:1258-65 (1993); London, S. J. et al., JAMA, 267:941-4 (1992); Foote, F. W. et al., Annals of Surgery, 121:197-222 (1945); Wellings, S. R. et al., J. Natl. Cancer Inst. 55:231-243 (1975); Allred, D. C. et al., Endocrine-Related Cancer, 8:47-61 (2001); Tavassoli, F. A and Norris, H. J., Cancer, 65:518-29 (1990); Wellings et al., J. Natl. Cancer Inst. 55:231-273 (1975); Page D. L. and Dupont W. D., Breast Cancer Research and Treatment, 28:157-166 (1993); Guray M. and Sahin A. A., Oncologist, 11:435-449 (2006). Taken together, histological and epidemiological evidence points to atypical as well as non-atypical hyperplastic lesions as the earliest precursor lesions that have significantly increased potential for developing IBC.

It is estimated that about 800,000 to 1 million breast biopsies are performed per year in the United States for a suspected tumor or a growth condition, and of these, only about 200,000 to 225,000 turn out to be cancerous; the rest are non-cancerous benign tumors. Among the non-cancerous tumors, about half are true benign and pose little risk. The remaining half of the non-cancerous tumors are proliferative tumors of atypical and non-atypical types. Although not all atypical or non-atypical proliferative lesions progress to IBC, a significant number of women diagnosed with proliferative tumors develop cancer. One study found that approximately 20% of subjects diagnosed with atypical hyperplasias subsequently developed cancer in 1-5 or more years. Among the non-atypical proliferative tumor group that included usual hyperplasias, papillomas and Sclerosing adenosis, approximately 10% developed cancer in 1-5 or more years (Hartman et al., New England J. Med, 353: 229-237 (2005)). Follow up studies estimated that of the approximately 300,000-400,000 proliferative tumors diagnosed every year in the United States, approximately 40,000 develop into IBC after 1-5 or more years (Worsham et al., Breast J., 13:116-121 (2007); Coopey et al., Breast Cancer Res. And Treatment, 10549-012, 2318(2012)). Therefore, it would be advantageous to stratify the approximately 40,000 subjects who will progress to cancer and target them for prophylactic treatments to prevent breast cancer from developing.

Thus, there is a need for improved materials and method for assessing early hyperplastic lesions, the presence of which in a subject is a significant indicator that a subject will eventually develop invasive breast cancer. Embodiments of the present disclosure described herein provide such improvements.

SUMMARY

Embodiments of the present disclosure include a method of predicting cancer in a subject. In accordance with these embodiments, the method includes quantifying levels of at least two oncogenic biomarkers or fragments thereof from a hyperplastic tissue sample from a subject; calculating a risk score based on the levels of the at least two oncogenic biomarkers or fragments thereof; and determining that the subject has a low, intermediate or high risk of developing cancer based on the calculated risk score. In some embodiments, one of the at least two oncogenic biomarkers is selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

Embodiments of the present disclosure also include a biomarker panel for determining cancer risk in a subject. In accordance with these embodiments, the panel includes at least two of the following oncogenic biomarkers: HEC1, CEACAM6, HYAL1, and MMP-1; wherein quantification of levels of one of the at least two oncogenic biomarkers or fragments thereof is used to calculate a risk score predictive of a low, intermediate, or high risk of developing cancer.

Embodiments of the present disclosure also include a method of classifying a patient who may be at risk of developing cancer. In accordance with these embodiments, the method includes quantifying levels of at least two oncogenic biomarkers or fragments thereof from a hyperplastic tissue sample from a subject; calculating a risk score based on the levels of the at least two oncogenic biomarkers or fragments thereof; and classifying the subject as having a low, intermediate or high risk of developing cancer based on the calculated risk score. In some embodiments, one of the at least two oncogenic biomarkers is selected from the group consisting of HEC1, CEACAM6, HYAL1, and MMP-1.

BRIEF DESCRIPTION OF THE DRAWINGS

FIGS. 11A-11B include representative Receiver Operating Characteristic (ROC) curves drawn for the combined expression levels of one of the triplets (FIG. 11A) or the combination of all four oncoproteins (FIG. 11B), MMP-1, CEACAM6, HYAL1, and HEC1; AUC is shown for both FIG. 11A and FIG. 11B.

FIGS. 12A-12B include representative scatter plots of Risk Scores that were computed from the expression levels of one of the triplets (FIG. 12A) or the combination of all four oncoproteins (FIG. 12B), CEACAM6, HYAL1, MMP-1, and HEC1, in tissues of subjects who subsequently developed cancer in one or more years (test case tissues; red triangles) and in tissues from subjects who did not develop cancer in five or more years (control tissues; blue circles).

FIGS. 13A-13B include representative graphs demonstrating the densities of Risk Scores computed from the expression levels of one of the triplets (FIG. 13A) or the combination of all four oncoproteins (FIG. 13B), CEACAM6, HYAL1, MMP-1, and HEC1, in tissues from subjects who did not develop cancer in five or more years (control tissues; blue line) and in tissues of subjects who subsequently developed cancer in one or more years (test case tissues; red line).

FIGS. 14A-14C include representative graphs demonstrating cancer free survival rates in years after precancerous biopsy based on Risk Scores computed from the expression levels of various combinations of the four oncoproteins, MMP-1, CEACAM6, HYAL1, and HEC1 among precancerous subjects. FIG. 14A is a representative graph demonstrating cancer free survival rates in years after precancerous biopsy based on Risk Scores computed from the expression levels of one of the duplets of the four oncoproteins, CEACAM6, HYAL1, MMP-1, and HEC1 among precancerous subjects. FIG. 14B is a representative graph demonstrating cancer free survival rates in years after precancerous biopsy based on Risk Scores computed from the expression levels of one of the triplets of the four oncoproteins, CEACAM6, HYAL1, MMP-1, and HEC1 among precancerous subjects. FIG. 14C is a representative graph demonstrating cancer free survival rates in years after precancerous biopsy based on Risk Scores computed from the expression levels of the combination of all four oncoproteins, CEACAM6, HYAL1, MMP-1, and HEC1 among precancerous subjects.

FIGS. 17A-17B includes representative graphs of CEACAM6 (FIG. 17A) and MMP-1 (FIG. 17B) mRNA expression levels measured by RT-QPCR in DCIS tumors (orange bars), invasive breast cancer (IBC) tumors (red bars) and ductal lavage (DL) samples (DL cells from cancer patients (black/red bars), atypical DL cells (pink bars) and benign DL cells (green bars).

DETAILED DESCRIPTION

Figure 1:
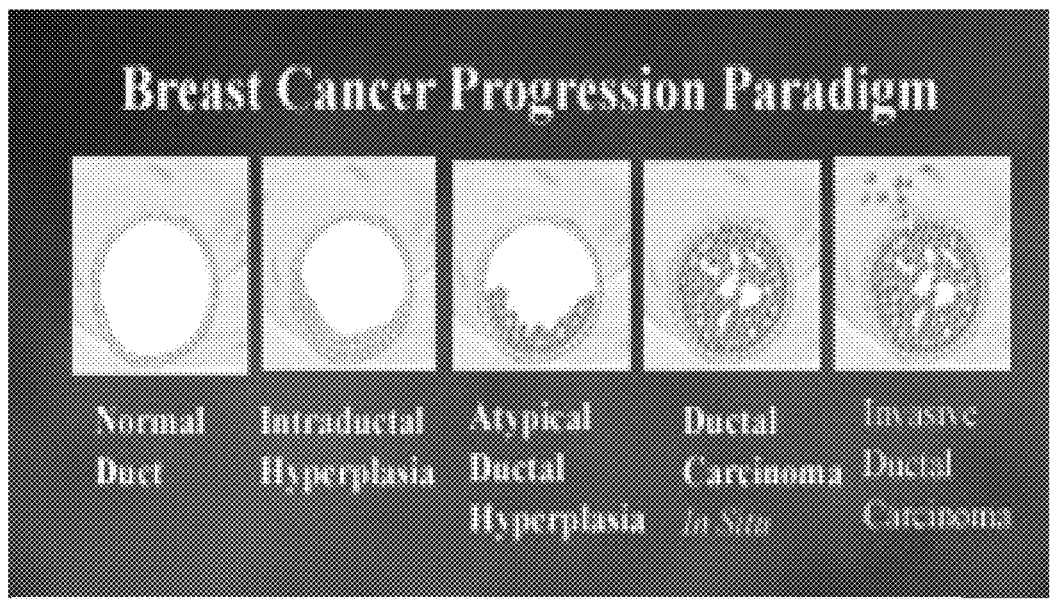
FIG. 1 includes representative images of the stages of breast cancer progression from normal breast epithelium to cancer via intermediate stages of hyperplasia, followed by atypical hyperplasia and ductal carcinoma in situ (DCIS) and Invasive Breast Cancer (IBC).

The present disclosure relates generally to determining the risk of developing breast cancer. In particular, the present disclosure provides materials and methods for determining whether a subject diagnosed with a non-cancerous breast tumor will develop cancer based on expression of multiple oncogenic biomarkers in the non-cancerous breast tumor. The present disclosure also provides a cancer risk score to determine whether a subject has low risk, intermediate risk, or high risk of developing cancer, thereby permitting selection of appropriate therapies to treat the subject.

Section headings as used in this section and the entire disclosure herein are merely for organizational purposes and are not intended to be limiting.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

"Antibody" and "antibodies" refer to monoclonal antibodies, multispecific antibodies, bifunctional antibodies, human antibodies, humanized antibodies (fully or partially humanized), animal antibodies (such as, but not limited to, antibodies obtained or derived from a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (see, e.g., Wu et al., *Nature Biotechnology*, 25(11): 1290-1297 (2007), and International Patent Application Publication No. WO 2001/058956)), and functionally active epitope-binding fragments of any of the above. The term "bifunctional antibody," as used herein, refers to an antibody that comprises a first arm having a specificity for one antigenic site and a second arm having a specificity for a different antigenic site, i.e., the bifunctional antibodies have a dual specificity.

The terms "antibody fragment" and "antibody fragments" refer to a portion of an intact antibody comprising the antigen-binding site or variable region. The portion does not include the constant heavy chain domains (i.e., CH2, CH3 or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

As used herein, the term "biomarker" refers to a measurable substance, the detection of which indicates a particular disease or risk of acquiring a particular disease. A "biomarker" may indicate a change in expression or state of the measurable substance that correlates with the prognosis of a disease. A "biomarker" may be a protein or peptide, a nucleic acid, or a small molecule. A "biomarker" may be measured in a bodily fluid such as plasma, and/or in a tissue (e.g., mammary tissue). In the context of the method described herein, a "biomarker" can be an oncogenic polypeptide or nucleic acid (e.g., estrogen receptor).

As used herein, "diagnosis" and similar terms refer to the identification of a particular disease.

"Label" and "detectable label" generally refers to a moiety attached, directly or indirectly, to an analyte-binding molecule (e.g., antibody or analyte-reactive fragment thereof) or an analyte to render the reaction between the analyte-binding molecule (e.g., antibody or analyte-reactive fragment thereof, a nucleic acid probe, etc.) and the analyte detectable, and the an analyte-binding molecule (e.g., antibody or analyte-reactive fragment thereof) or analyte so labeled is referred to as "detectably-labeled." A label can produce a signal that is detectable, such as by visual or instrumental means. In some aspects, a label can be any signal-generating moiety, and sometimes is referred to herein as a reporter group. As used herein, the label (or signal-generating moiety) produces a measurable signal which is detectable by external means, such as by the measurement of electromagnetic radiation, and, depending on the system employed, the level of signal can vary to the extent the label is in the environment of the solid support (e.g., an electrode, microparticle or bead).

"Predetermined cutoff," "cutoff," "predetermined level," and "reference level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). In some aspects, the present disclosure provides exemplary predetermined levels and reference levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "biological sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, mammary tissue, epithelial tissue, ascetic fluid, gynecological fluid, urine, peritoneal fluid, cerebrospinal fluid, a fluid collected by vaginal rinsing, or a fluid collected by vaginal flushing, breast tissue, ovarian tissue, brain tissue, bone tissue, genital tract tissue, gastrointestinal tract tissue, nervous system tissue, lung tissue, prostate tissue, and immune system tissue. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

As used herein, the terms "prognosis," "prognosticate," and related terms refer to the description of the likely outcome of a particular condition, such as invasive breast cancer (IBC). For example, in a subject with suspected IBC, measurement of the expression of certain oncogenes enables determination of risk of mortality, because the expression of certain oncogenes have been shown herein to correlate with an increased risk of mortality due to the development of IBC.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). In some aspects, the subject is a human.

The terms "treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

As used herein, the term "ductal lavage" refers to cells removed from the milk ducts of breasts. Generally, these cells can be obtained, for example, by inserting a thin flexible catheter into the milk duct opening in the nipple under local anesthesia and injecting normal saline and gently pushing the fluid to flush out the loose cells in the entire duct.

As used herein, "nipple discharge" refers to fluid oozing from the breasts without applying any mechanical force to expel the fluid.

As used herein, the terms "hyperproliferation," "hyperproliferative" and variations thereof generally refers to cells that have histologically normal nuclei but that divide or expand at a rate that is higher than normal cells.

As used herein, the term "benign" can be used to refer to cells or ducts in breast tissue expand at a faster than normal (e.g., benign hyperplasia), independent of the proliferation of the ductal epithelial cells.

As used herein, the term "atypical ductal hyperplasia" or "ADH" generally refers to a precancerous condition where the cells in the ducts are dividing at a faster rate than normal and have nuclei that appear histologically abnormal, but there are no cancerous cells. As used herein, the term "ADHC" generally refers to ADH subjects who subsequently developed cancer in 1-5 or more years after the diagnosis of ADH.

As used herein, the term "atypical lobular hyperplasia" or "ALH" generally refers to a precancerous condition where the cells in the lobules are dividing at a faster than normal rate and have nuclei that appear histologically abnormal but there are no cancerous cells. As used herein, the term "ALHC" generally refers to ALH subjects who subsequently developed cancer.

As used herein, the term "usual ductal hyperplasia" or "UDH" generally refers to a precancerous condition where cells of the ducts are dividing at a faster than normal rate and form several layers, and in some instances form tumors, but the nuclei of cells appear histologically normal. As used herein, the term "UDHC" generally refers to UDH subjects who subsequently developed cancer in 1-5 or more years after the diagnosis of UDH.

As used herein, "usual lobular hyperplasia" or "ULH" generally refers to a precancerous condition where lobular cells are dividing at a faster than normal rate and form several layers, and in some instances form tumors, but the nuclei of cells appear histologically normal.

As used herein, the term "papilloma" or "PAP" generally refers to a precancerous non-ADH hyperplasia of the breast ducts with papillary projections which are distinct from ADH, ALH and UDH.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. DETECTION OF ONCOGENIC BIOMARKERS

Figure 2:
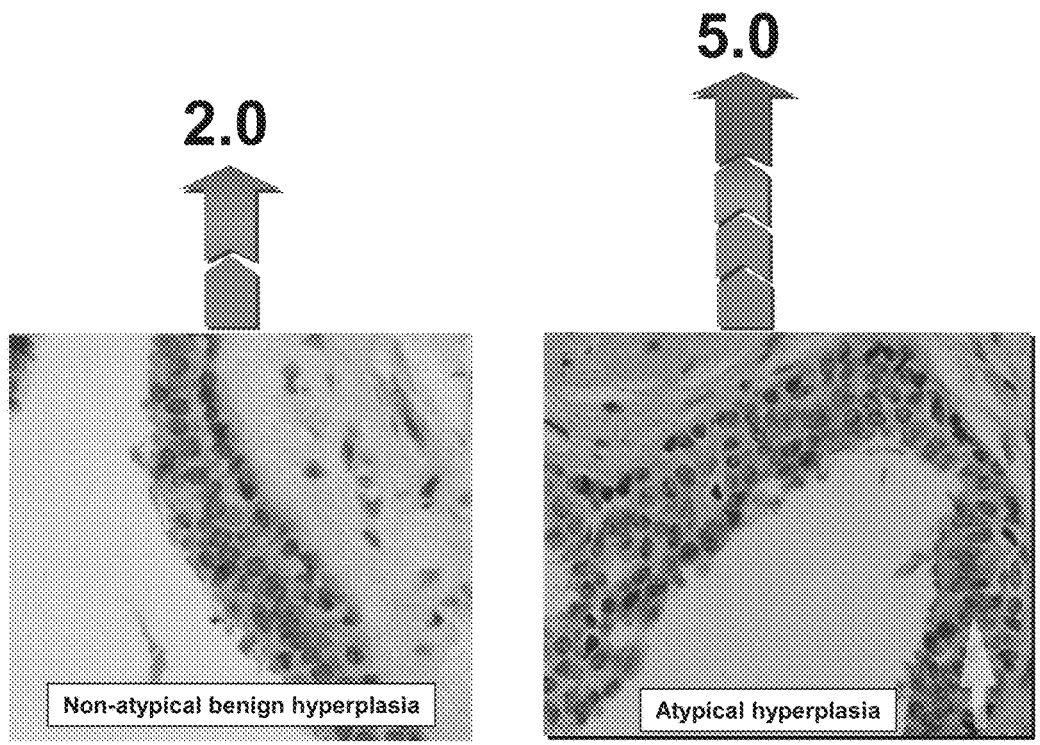
FIG. 2 includes representative histological images demonstrating increased risk for breast cancer among subjects diagnosed with non-atypical benign hyperplasia (two-fold increase) and subjects diagnosed with atypical hyperplasia (five-fold increase).
Figure 3:
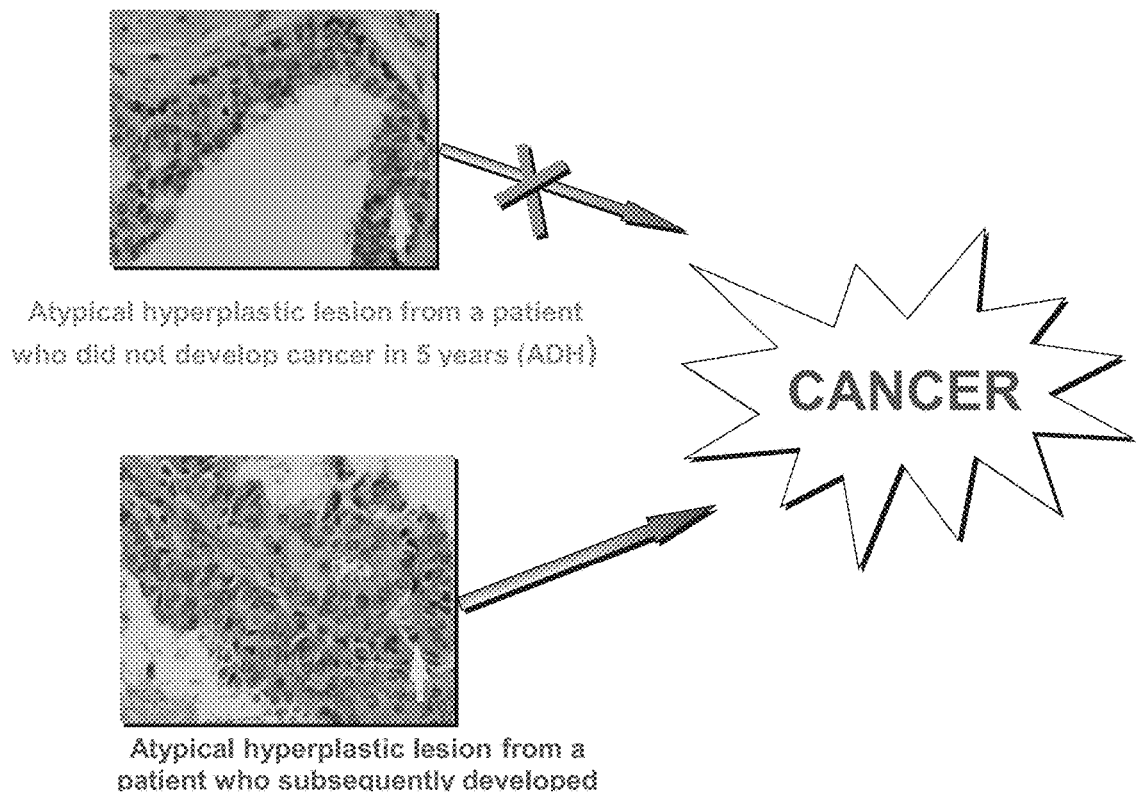
FIG. 3 includes representative histological images demonstrating the similar morphology between precancerous tumors from subjects who subsequently developed cancer and subjects who did not develop cancer in at least five years.

Histologically, proliferative tumors from subjects who subsequently develop cancer are not different from the tumors of subjects who will not subsequently develop cancer (e.g., see FIGS. 1-3). Thus, histology-based diagnoses are not a sufficient method for differentiating tumors that will subsequently develop into cancer from tumors that will not develop into cancer. Additionally, there are no current means for accurately identifying, and subsequently stratifying, patient populations having precancerous tumors that go on to develop breast cancer. The present disclosure addresses this need by providing the materials and methods for differentiating high risk candidates who will likely benefit from prophylactic therapies from low risk subjects who wish to avoid unnecessary therapeutic intervention.

Currently, preventive therapies, including Tamoxifen, Raloxifene, and/or Aromatase Inhibitors (AIs), are the standard recommended therapies for patients diagnosed with proliferative precancerous tumors (e.g., atypical hyperplasias, papillomas, sclerosing adenosis and usual hyperplasias). However, both patients and their oncologists are faced with the dilemma of whether to accept or forego these therapies because of the lack of any clinical methodology for precisely stratifying subjects according to cancer development risk. As a result, patients who have low cancer risk may be unnecessarily subjected to severe side effects of these prophylactic drugs (e.g., pulmonary embolism, deep vein thrombosis, stroke, endometrial cancers, cataracts, vasomotor instability, musculo-skeletal pain, bone loss, etc.). On the other hand, patients who have a high risk of developing cancer but choose not to receive prophylactic therapies may not receive the lifesaving treatment they need. Therefore, understanding the molecular and genetic mechanisms underlying how precancerous tumors progress to cancer will be important for designing clinical tests to stratify patients having precancerous tumors based on cancer risk, and will facilitate the development of novel molecular therapies.

Figure 4:
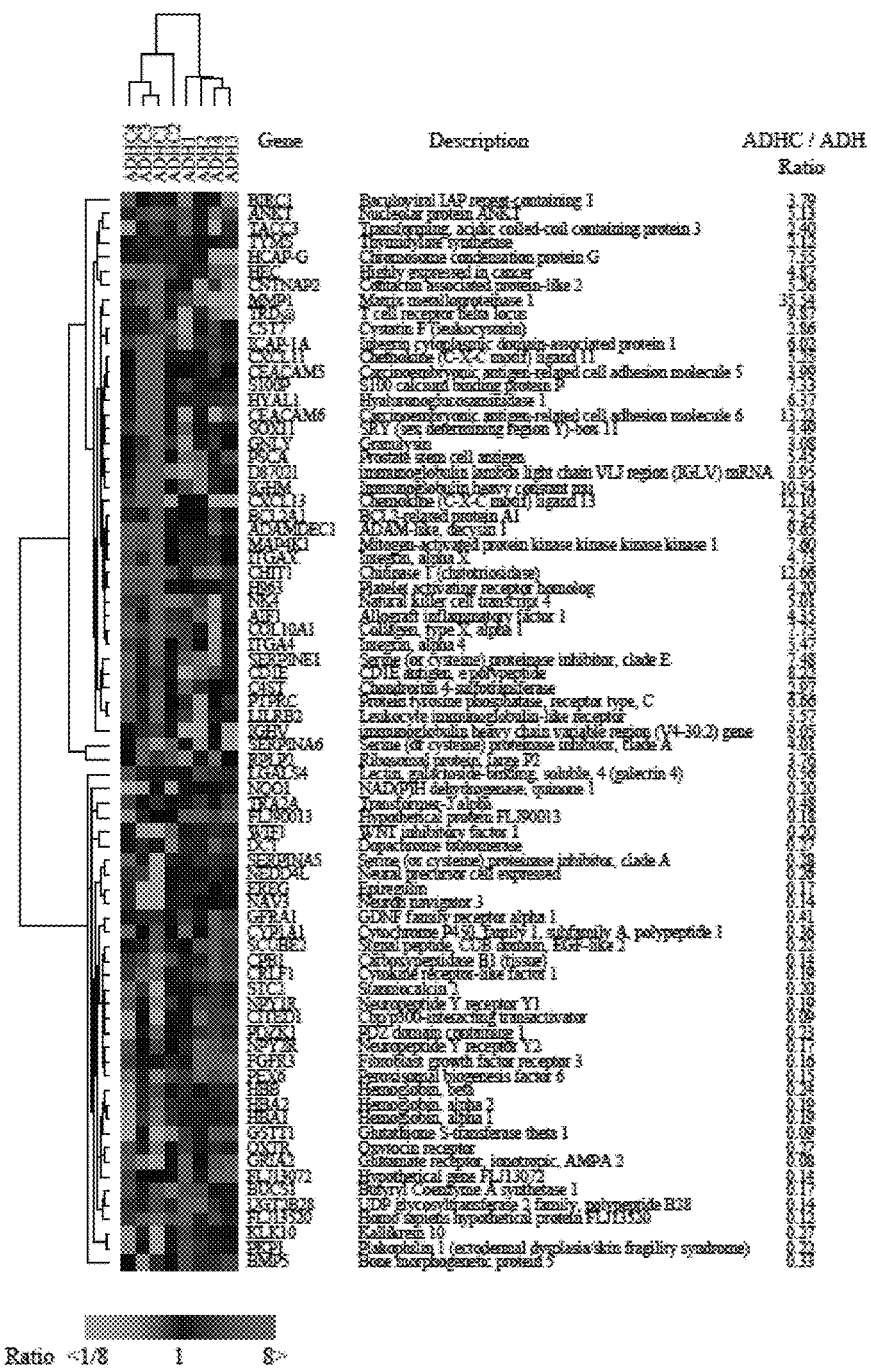
FIG. 4 is a representative heat map showing the top 30 upregulated and downregulated genes identified using microarray analysis in which atypical hyperplasias from subjects who subsequently developed breast cancer were compared to those who did not develop cancer.
Figure 5:
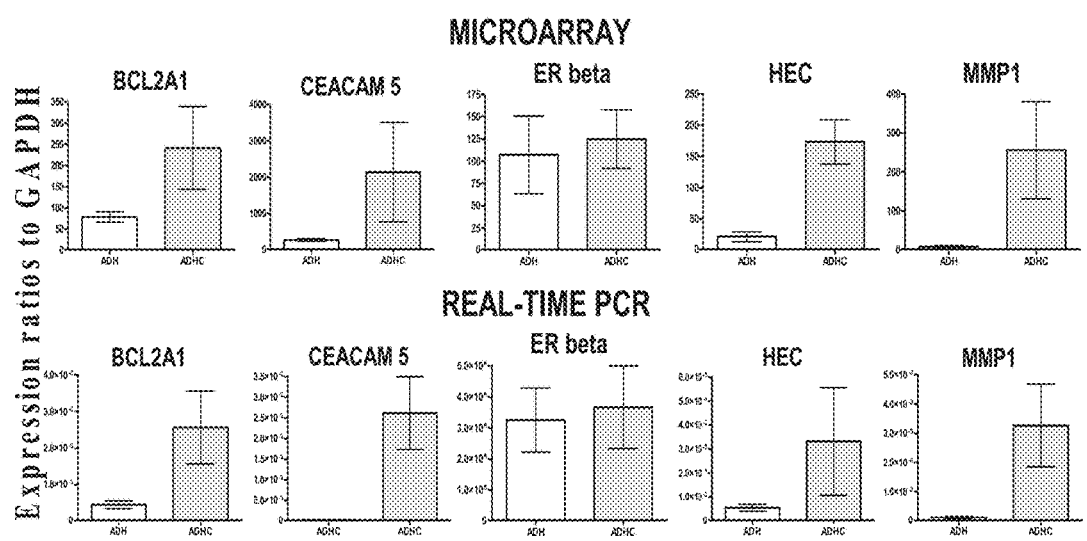
FIG. 5 includes representative bar graphs demonstrating the upregulation of four genes (BCL2 A1, CEACAM5, HEC1, and MMP-1) and one unchanged gene (Estrogen Receptor beta also called ESR2) based on mRNA levels using microarray analysis (upper panel) and RT-QPCR (lower panel) in atypical tissues from subjects who subsequently developed cancer (ADHC) compared to those who did not develop cancer (ADH).

The present disclosure provides materials and methods for differentiating between precancerous tissues of subjects who are likely to develop cancer from those who are not likely to develop cancer. Embodiments of the present disclosure provide analysis of the gene expression patterns in various types of precancerous tumor tissues, and identified that the expression of certain cancer genes were elevated in precancerous tumor tissues in subjects who subsequently developed cancer as compared to those who did not develop cancer (FIG. 4). For example, four genes, BCL2A1, CEACAM5, HEC1, and MMP-1, were found to be significantly upregulated in precancerous tumor tissues in patients who developed cancer as compared to those who did not develop cancer, and were also undetectable in non-hyperplastic tissue (FIG. 5).

Embodiments of the present disclosure provide a biomarker-based diagnostic test that can predict the likelihood of developing breast cancer for subjects who develop noncancerous but proliferative breast tumors such as atypias, and non-atypias (e.g., usual hyperplasias, papillomas, scherosing adenosis). In addition, the present disclosure provides the methods for identifying molecular targets to facilitate the design of novel prophylactic drugs to treat precancerous tumors and prevent IBC development.

Embodiments of the present disclosure provide methods for predicting cancer in a subject by detecting expression of various oncogenic markers, including HEC1 (Highly Expressed in Cancer protein), CEACAM6 (Carcino Embryonic Antigen Cell Adhesion Molecule 6), HYAL1 (Hyaluronoglucosaminidase 1), MMP-1 (Matrix Metalloproteinase-1), and any combination thereof. In some embodiments, methods can include detecting expression levels of one, two, three, or all four of these oncogenic biomarkers. In some embodiments, methods can include detecting expression levels of two of the four oncogenic biomarkers, and in other embodiments, methods include detecting three of the four oncogenic biomarkers (i.e., a triplet). In still other embodiments, the methods include detecting one or more of these four oncogenic biomarkers, in addition to other oncogenic biomarkers known to one of ordinary skill in the art based on the present disclosure.

Detection of oncogenic biomarkers, such as HEC1, CEACAM6, HYAL1, and MMP-1 include obtaining a tissue sample, including cells, from a subject. In some embodiments, the tissue sample is a hyperplastic tissue sample, such as hyperplastic tissue from a pre-cancerous tumor, or the tissue sample is atypical hyperplastic tissue, usual hyperplastic tissue, or a papilloma tissue. In some embodiments, hyperplastic tissue samples can be obtained from at least one of breast tissue, ovarian tissue, brain tissue, bone tissue, urinary tract tissue, kidney tissue, lymphatic tissue, blood, testicular tissue, genital tract tissue, gastrointestinal tract tissue, nervous system tissue, lung tissue, prostate tissue, head and neck tissue, and immune system tissue. In some embodiments, the tissue sample is from hyperplastic tissue obtained using at least one of a core biopsy, a surgical biopsy, a fine needle aspiration procedure, ductal lavage, a nipple aspirate fluid procedure, and nipple discharge collection. Other suitable tissue samples can be obtained from a subject for the purposes of practicing the methods as described herein. As defined above, suitable samples include, but are not limited to, blood, serum, urine, saliva, mammary tissue, pleural fluid, epithelial tissue, mammary epithelial tissue, and ductal tissue.

Oncogenic biomarkers can be assayed based on gene expression, such as by measuring mRNA levels by various means known in the art. Methods of measuring gene expression include, but are not limited to, PCR, quantitative PCR, digital PCR, reverse transcriptase PCR (RT-PCR), real time PCR (e.g., taq-man PCR), Northern blotting, gene chip analysis, micro-array analysis, and quantitative sequence analysis. Other means for measuring gene expression can also be used, as would be apparent to one of ordinary skill in the art based on the present disclosure, including physical and molecular biology methods. For example, suitable physical methods include mass spectrometric methods, fluorescence resonance energy transfer (FRET) assays, chromatographic assays, and dye-detection assays. Suitable molecular biology methods include, but are not limited to, Southern blot hybridization, nucleic acid dot- or slot-blot hybridization, in situ hybridization, nucleic acid chip assays, and the like. Other methods to detect biomarkers include, e.g., nuclear magnetic resonance (NMR), fluorometry, colorimetry, radiometry, luminometry, or other spectrometric methods, plasmon-resonance (e.g. BIACORE), and one- or two-dimensional gel electrophoresis.

Oncogenic biomarkers can be assayed based on protein expression, such as by measuring protein levels, or byproducts or fragments of oncoproteins that are indicative of protein expression. Methods of measuring protein expression of the various oncoproteins of the present disclosure can be performed using any suitable assay known in the art. Examples of suitable assays include, but are not limited to, immunoassay, such as sandwich immunoassay (e.g., monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, and the like. Other means for measuring protein expression can also be used, as would be apparent to one of ordinary skill in the art based on the present disclosure.

Immunoassay methods for measuring protein expression and/or activity of the oncoproteins of the present disclosure can be carried out in any of a wide variety of formats, descriptions of which are provided in, e.g., Asai, ed., *Methods in Cell Biology Volume 37: Antibodies In Cell Biology*, Academic Press, Inc. New York (1993), and Stites & Ten, eds., *Basic and Clinical Immunology 7th Edition*, (1991). Other assay formats which may be used in connection with the method described herein include, for example, a rapid test, a Western blot, as well as the use of paramagnetic particles in, for example, an ARCHITECT® assay (see Frank Quinn, *The Immunoassay Handbook*, Second edition, edited by David Wild, pp. 363-367 (2001)), and other appropriate formats known to those of ordinary skill in the art.

In some embodiments, immunohistochemistry (IHC) can be used to detect the expression of various oncogenic biomarkers and can be the basis for determining cancer risk, as described herein. Generally, IHC combines anatomical, immunological and biochemical techniques to identify discrete tissue components by the interaction of target antigens with specific antibodies tagged with a visible label. IHC enables visualization of the distribution and localization of specific cellular components within cells and in the proper tissue context, as well as the expression of various oncoproteins. IHC involves obtaining tissue samples, which are prepared on individual slides, or multiple samples can be arranged on a single slide for comparative analysis, such as with tissue microarrays. IHC slides can be processed and stained manually, while technological advances now provide automation for high-throughput sample preparation and staining. Samples can be viewed by light or fluorescence microscopy, for example, and images can be captured and quantitated (e.g., multiparametric IHC data). Patient or animal biopsies, or whole animal organs, can be collected for preservation and IHC analysis, depending on the requirements of the assay. Tissue must generally be rapidly preserved to prevent the breakdown of cellular protein and tissue architecture. Often, the tissue is perfused, or rinsed of blood, prior to preservation to prevent the detection of hematologic antigens that may interfere with the detection of target antigens. Tissue perfusion can be performed on anesthetized animals by using a peristaltic pump to exsanguinate the animal and rinse the vasculature with sterile saline to remove all blood components from the entire animal. After sectioning the tissue, the target organ or tissue can then be collected for IHC. Detecting the target antigen with antibodies is a multi-step process that requires optimization at every level to maximize the signal detection. Both primary and secondary antibodies can be diluted into a buffer to help stabilize the antibody, promote the uniform dissemination throughout the sample and discourage nonspecific binding. While one diluent may work with one antibody, the same diluent may not work with another antibody, demonstrating the need for optimization for each antibody. IHC target antigens can be detected through either chromogenic or fluorescent means, and the type of readout depends on the experimental design. For fluorescent detection, the reporter that the primary or secondary antibody is conjugated to is a fluorophore that is detected by fluorescent microscopy. Chromogenic detection is based on the activities of enzymes, most often horseradish peroxidase (HRP) or alkaline phosphatase (AP), which form colored, insoluble precipitates upon the addition of substrate, such as DAB and NBT/BCIP, respectively. Other variations of IHC protocols and procedures can be used with the methods described herein, as would be recognized by one of ordinary skill in the art based on the present disclosure.

In some embodiments, analysis of mRNA can be used to detect, measure, and/or quantify the expression or level of expression of various oncogenic biomarkers and can be the basis for determining cancer risk, as described herein. Non-limiting examples of mRNA analysis methods include reverse transcription-polymerase chain reaction (RT-PCR), competitive RT-PCR, real-time RT-PCR, RNase protection assay (RPA), Northern blotting, next generation sequencing, microarray analysis, and a DNA chip. In the present disclosure, the formulation for measuring the level of mRNA may be antisense oligonucleotides, primer pairs, or probes.

The elements of the assays described above can also be used in the form of a kit. The kit may also comprise one or more containers (e.g., vials, bottles, or strips) comprising the assay components and reagents needed for performing the assay (e.g., washing, processing, and indicator reagents).

3. DETERMINING INCREASED RISK OF DEVELOPING CANCER

Embodiments of the present disclosure provide methods for determining risk, including methods for determining risk of pre-cancerous tumors developing into cancer, and methods of determining cancer free survival rates, all of which are based on the expression levels of the various oncogenic biomarkers described herein. In certain embodiments, methods of predicting cancer in a subject include calculating a risk score based on the expression of two or more oncogenic biomarkers, such as HEC1, CEACAM6, HYAL1, and MMP-1. In other embodiments, methods of predicting cancer in a subject include calculating a risk score based on the expression of three or more oncogenic biomarkers, such as HEC1, CEACAM6, HYAL1, and MMP-1. In certain other embodiments, methods of predicting cancer in a subject include calculating a risk score based on the expression of four oncogenic biomarkers, such as HEC1, CEACAM6, HYAL1, and MMP-1.

In some embodiments, methods of predicting cancer in a subject include calculating a risk score based on the expression of one or more oncogenic biomarkers, such as HEC1, CEACAM6, HYAL1, and MMP-1, as described herein. In some embodiments, risk scores can be generated based on the expression levels of these oncogenic markers using logistic regression that includes quantifying immunohistochemical (IHC) grades for each marker for a plurality of samples using logistic regression to obtain coefficients for each marker, and then multiplying IHC grades of each marker with its respective regression coefficient for each sample and obtain values, followed by adding the obtained values of all the markers in a sample to derive "Composite Risk Score" for the combination of the oncogenic biomarkers.

In accordance with these methods, risk scores for various subject populations can be collected and stored in databases that can serve as tools for determining cancer risk, or for predicting the likelihood that an individual will develop cancer. In some embodiments, methods of the present disclosure include categorizing a risk score of an individual as low risk, intermediate risk, or high risk, based at least in part on comparing the individual's risk score, or underlying oncogenic marker expression data, to the appropriate database of risk scores or expression data. In some embodiments, a risk score equal to or less than 1 indicates a low risk of the subject developing cancer, a risk score greater than 1 but equal to or less than 5 indicates an intermediate risk of the subject developing cancer, and a risk score of greater than 5 indicates a high risk of the subject developing cancer (see, e.g., FIGS. 14A-14C).

In some embodiments, risk scores calculated based on the expression of the various oncogenic biomarkers described herein can be used to predict or calculate cancer free survival rates. To derive "Risk Prediction Probability Scores" (average risk scores) and % accuracy to predict risk, the distributions of risk scores (scaled from 0-10) of Controls and Test Cases can be using scattered plots and density plots (FIGS. 12A-12B and FIGS. 13A-13B). From the risk score distribution plots, estimates of scores that predict the probability of cancer development and 95% confidence Intervals can be calculated. From the risk score distribution data of Controls and Test Cases, cancer predictability rates can be determined with a margin of error and significance level. In some embodiments, a risk score categorized as low indicates that the subject has a cancer free survival rate of at least 95% for at least 19 years, wherein a risk score categorized as intermediate indicates that the subject has a cancer free survival rate of at least 80% at least 5 years, and wherein a risk score categorized as high indicates that the subject has a cancer free survival rate of at most 45% in the first 5 years.

In some embodiments, the methods described herein can be used to not only identify a subject who, for example, is at a high risk of developing cancer, but these methods can be used as part of prophylactic therapy to treat the subject. For example, a subject who is at high risk for developing cancer based on expression levels of the various oncogenic markers described herein can be treated with a therapeutic anti-cancer agent, in some cases, earlier than the subject otherwise would be treated if diagnosed with conventional means. Prophylactic therapies can include, for example, pharmaceutical agents and/or surgical therapies that are known to those of ordinary skill in the art. Pharmaceutical agents can include, for example, tamoxifen, raloxifen, and/ or an aromatase inhibitor. Surgical therapy can include, for example, a single or double mastectomy.

In some embodiments, the methods of the present disclosure can be used to identify, design or develop novel cancer therapies, such as novel therapeutic agents to treat cancer. For example, embodiments can include treating hyperplastic tissue and/or cells of hyperplastic tissue with a potential anti-cancer agent and determining expression levels of the various oncogenic markers described herein after treatment with the agent. If the expression of these biomarkers is reduced, the potential anti-cancer agent can be further tested for safety and efficacy. These oncogenic markers can also be used as part of a high throughput drug screening platform designed to assay large numbers of small molecule drugs for their potential anti-cancer properties.

4. PATIENT MONITORING

Embodiments of the present disclosure include monitoring a subject who may be at risk for developing cancer. The subject may be a patient who has not been diagnosed as having cancer, but may be at risk of developing cancer due to various clinical or medical assessments (e.g., family history, histological evaluation, genetic evaluation, and environmental factors). In other embodiments, the subject may have been diagnosed as having a precancerous tumor or precancerous hyperplasia, but has not yet developed cancer. In accordance with these embodiments, the method includes obtaining a tissue sample, such as a precancerous hyperplastic tissue sample, from a subject and quantifying levels of expression of one or more of the oncogenic biomarkers using the methods disclosed herein. Additionally, the method also include calculating a risk score based on the levels of expression of one or more of the oncogenic biomarkers as disclosed herein. The hyperplastic tissue sample can be obtained directly from the subject, or the hyperplastic tissue sample can be obtained from hyperplastic tissue that has been surgically removed via a biopsy from the subject.

In some embodiments, the method includes evaluating a subject to determine whether an anti-cancer treatment should be administered, or to determine whether to alter a current course of anti-cancer treatment. For example, a subject may be assigned a risk score based on the expression levels of one or more of the oncogenic biomarkers (e.g., at least two oncogenic biomarkers) in a hyperplastic tissue sample from the subject. Based on the risk score, a determination can be made as to the type of anti-cancer treatment regimen that should be administered to the subject. In some cases, a subject that has been evaluated as having an intermediate or high risk of developing cancer may be administered an anti-cancer treatment to prevent the development of cancer, whereas a subject evaluated as having a low risk of developing cancer will not be administered anti-cancer treatment.

In some embodiments, the method includes obtaining a second tissue sample from the subject in order to evaluate whether a current course of anti-cancer treatment is effective. The tissue sample may be hyperplastic tissue or non-hyperplastic tissue. For example, a subject may be assigned a risk score based on the expression levels of one or more of the oncogenic biomarkers (e.g., at least two oncogenic biomarkers) in a second hyperplastic tissue sample (or non-hyperplastic tissue sample) from the subject, and in some cases, after a given regimen of anti-cancer treatment has been administered to the subject. The risk score can be calculated based on a change in the expression levels of one or more of the oncogenic biomarkers; that is, the risk score can be based on increased or decreased expression of one of the oncogenic biomarkers as compared to the expression levels of the oncogenic biomarker(s) in the first hyperplastic tissue sample. The risk score can also be calculated based on the expression of one of the oncogenic biomarkers from the second hyperplastic or non-hyperplastic tissue sample from the subject, and in some cases, subsequently compared to the risk score calculated based on the first hyperplastic tissue sample. Any changes in the risk scores can then be compared or evaluated to determine whether to (i) discontinue use of the anti-cancer agent in the subject; (ii) continue treatment with the anti-cancer agent in the subject; or (iii) administer a different anti-cancer agent to the subject based on the comparison of the first and second risk scores. For example, treatment with the anti-cancer agent may be discontinued because the second risk score is lower than the first risk score. The treatment with the anti-cancer agent may be continued because the first and second risk scores are identical. Or the treatment with the anti-cancer agent may be discontinued, and treatment with a new anti-cancer agent may be administered to the patient because the second risk score is higher than the first risk score.

5. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Several interconnected pathways can be dysregulated in precancerous tissues from subjects who subsequently developed cancer. For example, growth factor-mediated pathways known to be involved in tumor progression are the major pathways dysregulated in ADHC, including those that regulate cell surface stability, adhesion, motility (e.g., CEACAM6, Fibronectin) and promote cell migration, all of which are disrupted in ADHC. Additionally, CXCR4 pathways, which are involved in tumor progression, angiogenesis, metastasis, and survival pathways, are also affected in ADHC. Other disrupted pathways include WNT, PTPRC, and CD40 signaling pathways. All the disrupted pathways are known to promote cancer progression. Based on the disrupted pathways mapped, it is evident that ADHC tissues have several dysregulated cellular processes that would drastically derail cellular equilibrium and foster initiation of cancer development.

Example 2

Figure 6:
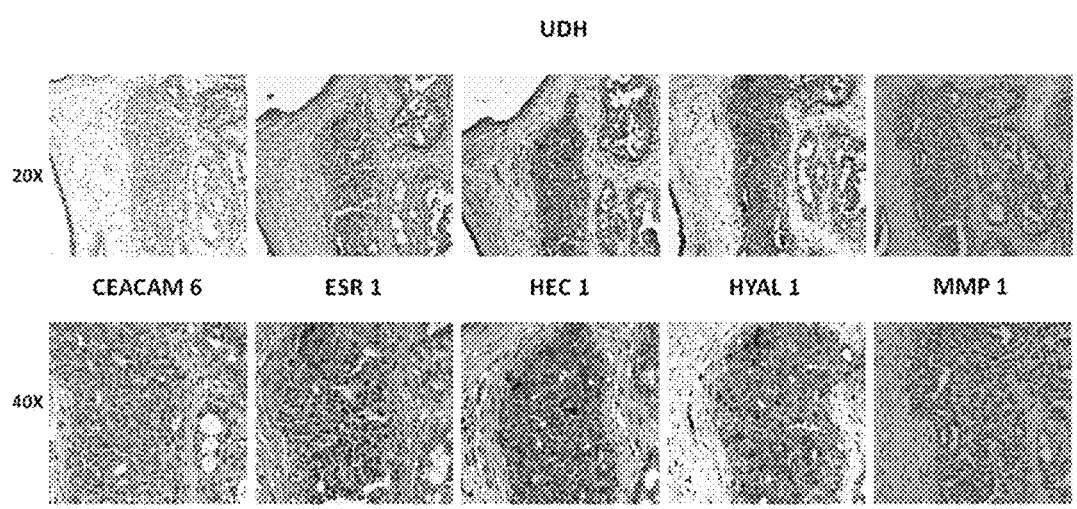
FIG. 6 includes representative images of the expression of cancer markers, CEACM6, HEC1, HYAL1, MPP-1, and ER in usual hyperproliferative condition (Usual Ductal Hyperplasia (UDHC) without atypia) of the breast from subjects who subsequently developed cancer.
Figure 7:
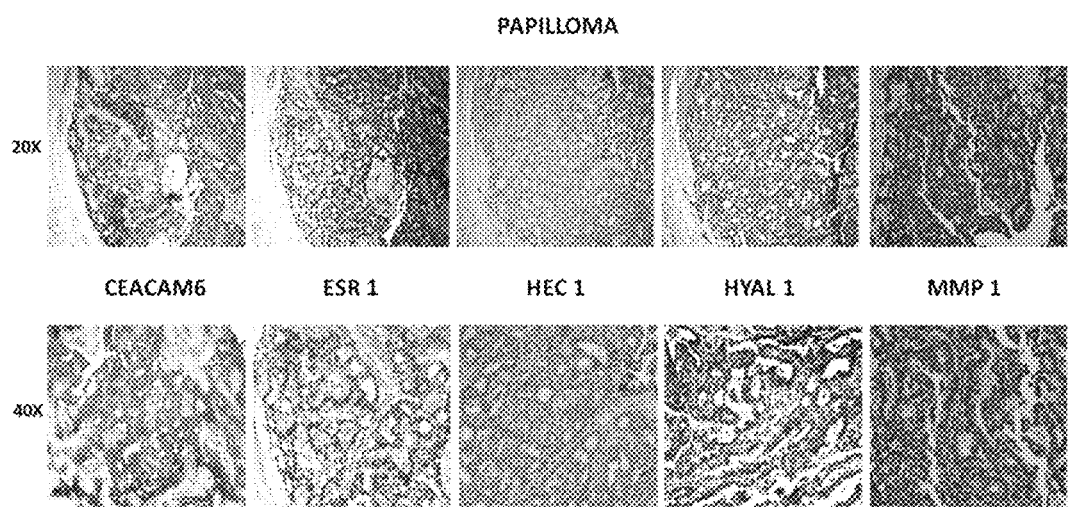
FIG. 7 includes representative images of the expression of cancer markers, CEACM6, HEC1, HYAL1, MPP-1 and ER in a papilloma type of hyperproliferative condition of the breast without atypia from subjects who subsequently developed cancer.
Figure 8:
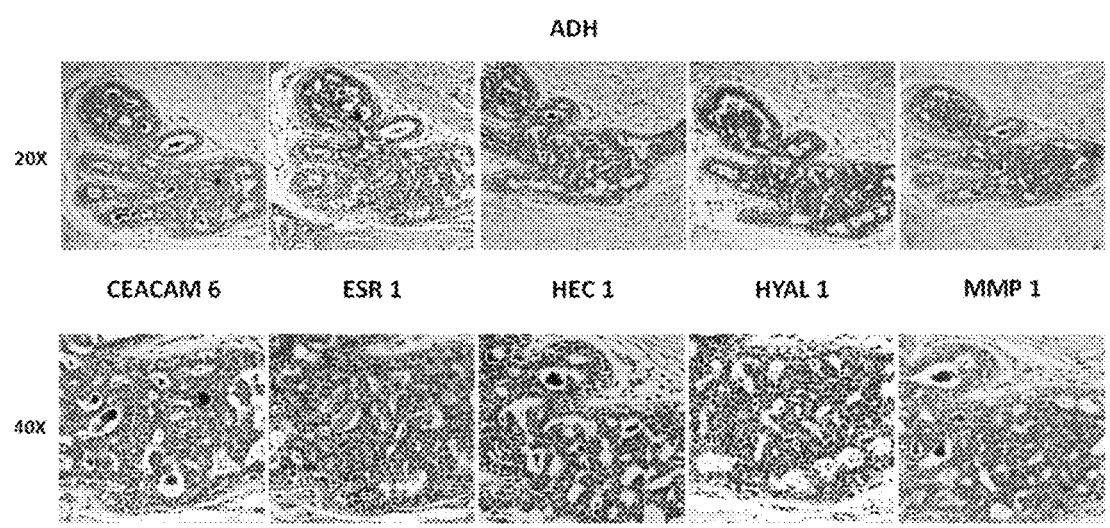
FIG. 8 includes representative images of the expression of cancer markers, CEACAM6, HEC1, HYAL1, and ER in an atypical type hyperproliferative condition of the breast from subjects who subsequently developed cancer.
Figure 9:
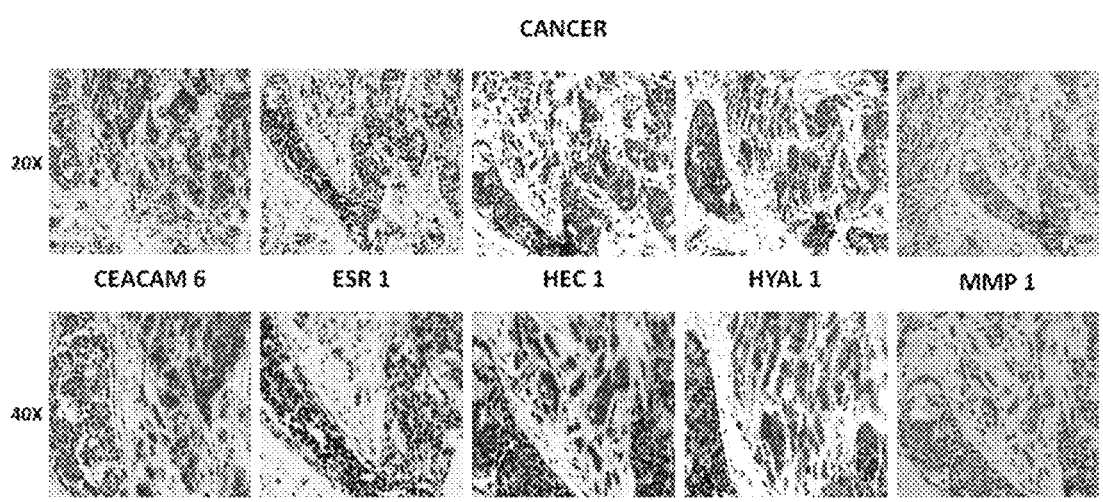
FIG. 9 includes representative images of the expression of cancer markers, CEACAM6, HEC1, HYAL1, MPP-1 and ER in cancerous condition of the breast.

Embodiments of the present disclosure have identified four genes, which include CEACAM6, HYAL1, MMP-1, and HEC1, that are upregulated in pre-cancerous tumors and that are correlated with an increased risk that those pre-cancerous tumors will develop into cancer. For example, gene expression studies that include microarray analysis (FIG. 4) and quantitative RT-PCR (FIG. 5) using ADHC tissue samples have demonstrated that these oncogenic markers are reliable predictors of cancer development. Protein levels of these oncogenic markers were also detected in Atypical hyperplastic tissues, Usual hyperplastic tissues, and papilloma type of hyperplastic tissues (FIGS. 6-8) from subjects who subsequently developed cancer in 1-5 years or more, at similar levels as cancer tissues (FIG. 9).

Example 3

In Table 1 below, Receiver Operating Characteristic Curves (ROC) statistical values, Sensitivity, Specificity, Positive Predictive Value (PPV) (correctly predicting cancer development in subjects who were positive for the markers), and Negative Predictive Value (NPV) (correctly predicting non-development of cancer in subjects who were negative for the markers) and P values were computed from expression levels of each of the four individual oncogenic biomarkers, one of the duplets, one of the triplets, and the combination of all four oncoproteins, CEACAM6, HYAL1, MMP-1 and HEC1. ROC analysis demonstrates that duplets of the four oncogenic markers were accurate predictors of the risk of cancer development in precancerous breast tissues.

TABLE 1

ROC Statistics values computed from Expression levels of each of the four oncoproteins, CEACAM6, MMP-1, HYAL1 and HEC1, a duplet, a triplet and the quadruplet.

| Marker | Sensitivity | Specificity | PPV | NPV | P value |
| --- | --- | --- | --- | --- | --- |
| HEC1 | 0.65 | 0.86 | 1 | 0.72 | 0.000763 |
| MMP-1 | 0.8 | 0.87 | 0.84 | 0.82 | $1.6 \times 10^{-6}$ |
| HYAL1 | 0.82 | 0.78 | 0.88 | 0.730 | $1.1 \times 10^{-6}$ |
| CEACAM6 | 0.69 | 0.86 | 0.67 | 0.87 | $3.0 \times 10^{-3}$ |
| One of the Duplets | 0.85 | 0.74 | 1 | 0.74 | $2.0 \times 10^{-4}$ |
| One of the Triplets | 0.81 | 0.77 | 0.88 | 0.84 | 0.00078 |
| Quadruplet | 0.84 | 0.82 | 0.83 | 0.88 | 0.00014 |

Example 4

Figure 10:
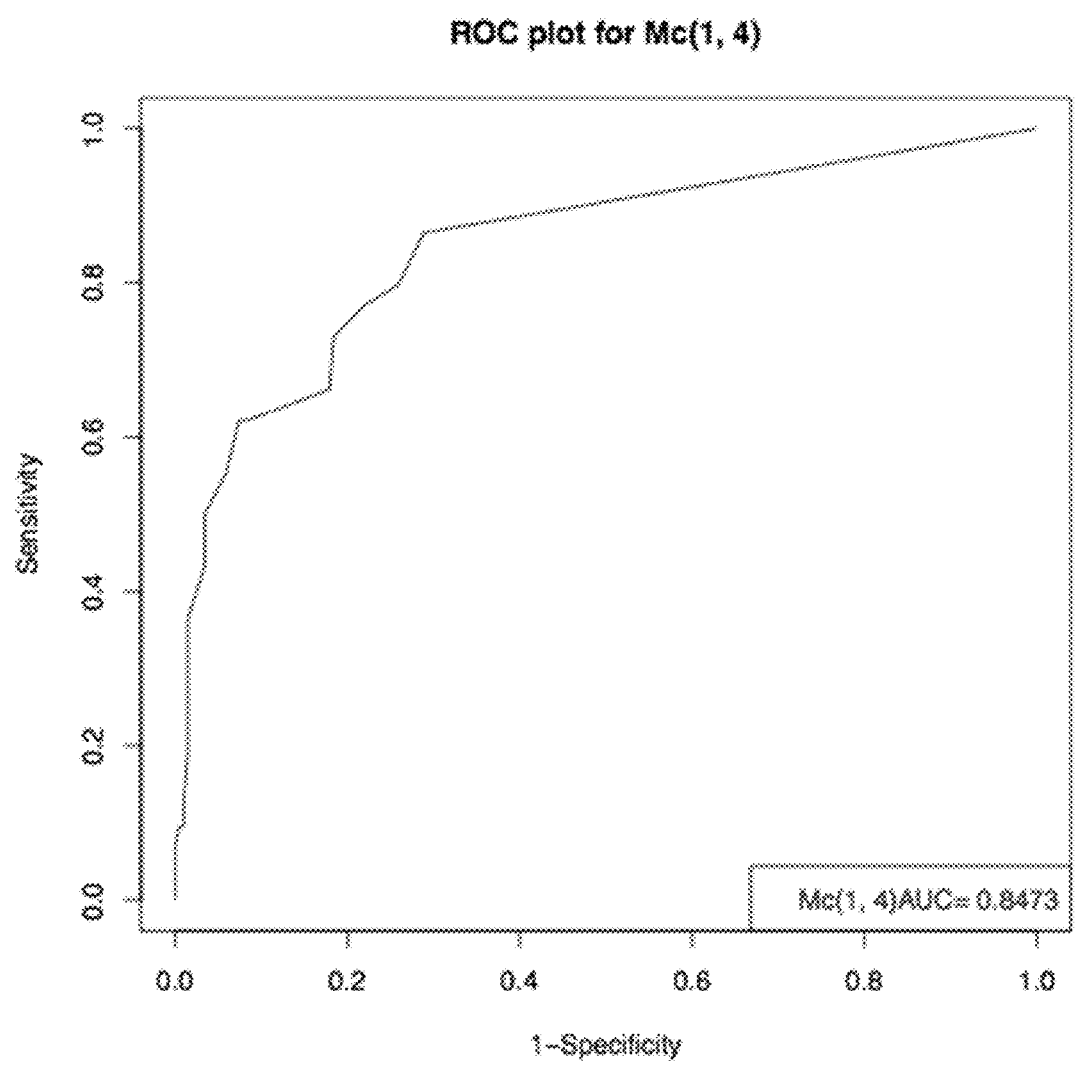
FIG. 10 is a representative Receiver Operating Characteristic (ROC) curve drawn for the combined expression levels of one of the duplets of the four oncoproteins, MMP-1, CEACAM6, HYAL1, and HEC1; AUC ("area under the curve") is shown.

As shown in FIG. 10, ROC curves drawn from the expression levels of one of the duplets of the four oncogenic markers, CEACAM6, HYAL1, MMP-1 and HEC1, gave an AUC of 0.8437, demonstrating that a duplet accurately predicts the risk of cancer development in precancerous breast tissues with at least 84% accuracy. As shown in FIG. 11A, ROC curves drawn from the expression levels of one of the triplets of the four oncogenic markers, CEACAM6, HYAL1, MMP-1 and HEC1, gave an AUC of 0.8709, demonstrating that a triplet accurately predicts the risk of cancer development in precancerous breast tissues with at least 87% accuracy. As shown in FIG. 11B, ROC curves drawn from the expression levels of the four oncogenic markers, CEACAM6, HYAL1, MMP-1 and HEC1, gave an AUC of 0.8983, demonstrating that these four markers together accurately predict the risk of cancer development in precancerous breast tissues with at least 89.83% accuracy.

Example 5

In Table 2 below, Risk Scores computed from the expression levels of one of the triplets of the four oncogenic markers, CEACAM6, HYAL1, MMP-1 and HEC1, in Test Case tissues that subsequently developed cancer are distinct from the controls that did not develop cancer for five or more years. These distinctions in Risk Scores allows for the stratification of subjects having pre-cancerous tumors into low, intermediate, and high risk groups, based on expression of triplets of these four oncogenic markers.

TABLE 2

Ranges of Risk Scores computed depending on the expression levels of one of the triplets of the four oncoproteins, CEACAM6, HYAL1, MMP-1 and HEC1 in precancerous tissues.

| Subjects who did not develop cancer in 5 or more years (Controls) | Subjects who subsequently developed cancer in one or more years (Cases) |
|---|---|
| 0.3-1.4 | 5.0-9.5 |

Example 6

As shown in FIGS. 12A-12B, Risk Scores computed from the expression levels of one of the triplets (FIG. 12A) or a combination of all four oncogenic markers (FIG. 12B), CEACAM6, HYAL1, MMP-1 and HEC1 in tissues from subjects who subsequently developed cancer in one or more years (Test Cases; red triangles) and in tissues from subjects who did not develop cancer in five or more years (Controls; blue circles) are segregated as shown in the scattered graph. These distinctions in Risk Scores allows for the stratification of subjects having pre-cancerous tumors into low, intermediate, and high risk groups, based on expression of at least triplet combinations of these four oncogenic markers.

Example 7

As shown in FIGS. 13A-13B, the densities of Risk Scores in Test Cases and Controls are shown. Risk Scores computed from the expression levels of one of the triplets (FIG. 13A) of the four oncogenic markers (FIG. 13B), CEACAM6, HYAL1, MMP-1 and HEC1, and from the combination of all four oncogenic markers, CEACAM6, HYAL1, MMP-1 and HEC1, in Control precancerous tissues are distinct from the Risk Scores from Test Case precancerous tissues. The Risk Score density in Control tissues is concentrated around the score of ≤1, whereas in Test Case tissues the Risk Scores densities are concentrated at ≥5 (of the total of 10). These distinctions in Risk Scores allows for the stratification of subjects having pre-cancerous tumors into low, intermediate, and high risk groups, based on expression levels of at least triplet combinations of these four oncogenic markers.

Example 8

The accuracy of correctly predicting the risk of cancer development based on the expression levels of one of the duplets, triplets, or the combination of all four oncogenic markers, HEC1, HYAL1, MMP-1, and CEACAM6 was calculated based on the formula below. Accuracy percentages were computed based on the prevalence of true positives and true negatives using the formula:

$$\text{Accuracy to predict the risk of cancer development} = \frac{a+d}{A+b+c+d}$$

where a, b, c, and d are:

| samples | True Positives | True Negatives |
|---|---|---|
| Cases positive | a | b |
| Cases negative | c | d |

The accuracy of correctly predicting the development of cancer in pre-cancerous tumors based on the expression level of at least duplet combinations of the four oncogenic markers, MMP-1, CEACAM6, HEC1 and HYAL1 was calculated based on data from 269 controls and 139 cases using the above formula was found to be approximately 82%. The accuracy of correctly predicting the development of cancer in pre-cancerous tumors based on the expression level of at least triplet combinations of the four oncogenic markers, MMP-1, CEACAM6, HEC1 and HYAL1, was calculated based on data from 255 controls and 130 cases using the above formula was found to be approximately 85%. The accuracy of correctly predicting the development of cancer in pre-cancerous tumors based on the expression level a combination of all four oncogenic markers, MMP-1, CEACAM6, HEC1 and HYAL1, was calculated based on data from 201 controls and 74 cases using the above formula was found to be approximately 87%.

Example 9

As shown in FIG. 14A, Kaplan Meier survival curves demonstrate that pre-cancerous subjects can be stratified into three groups based on risk scores computed from the expression levels of one of the duplet combinations of four oncoproteins, CEACAM6, HYAL1, MMP-1 and HEC1: 1) low risk group which has a risk score of ≤1; 2) intermediate risk group which has a risk of >1 and ≤5; and 3) elevated risk group which has a risk score of >5. The low risk group has a cancer free survival of over 95% for at least 19 years. The intermediate risk group has a cancer free survival of 95% for the first 5 years and decreases to ~75% after 10 years. For the elevated/high risk group which has a risk score of >5, cancer free survival in the first five years is at most ~45%, reduces to 20% in 10 years after precancerous biopsy.

As shown in FIG. 14B, Kaplan Meier survival curves demonstrate that pre-cancerous subjects can be stratified into three groups based on risk scores computed from the expression levels of one of the triplet combinations of four oncoproteins, CEACAM6, HYAL1, MMP-1 and HEC1: 1) low risk group which has a risk score of ≤1; 2) intermediate risk group which has a risk of >1 and ≤5; and 3) elevated risk group which has a risk score of >5. The low risk group has a cancer free survival of over 95% for at least 19 years. The intermediate risk group has a cancer free survival of 95% for the first 5 years, which decreases to ~75% after 10 years. For the elevated/high risk group, which has a risk score of >5, cancer free survival in the first five years is ~40%, which reduces to 20% in 10 years.

As shown in FIG. 14C, Kaplan Meier survival curves demonstrate that pre-cancerous subjects can be stratified into three groups based on risk scores computed from the expression levels of a combination of all four oncoproteins, CEACAM6, HYAL1, MMP-1 and HEC1: 1) low risk group which has a risk score of ≤1; 2) intermediate risk group which has a risk of >1 and ≤5; and 3) elevated risk group which has a risk score of >5. The low risk group has a cancer free survival of over 95% for at least 19 years. The intermediate risk group has a cancer free survival of 90% for the first 5 years, which decreases to ~65% after 10 years. For the elevated/high risk group which has a risk score of >5, cancer free survival in the first five years is ~40%, which reduces to 15% in 10 years after precancerous biopsy.

Additionally, as shown in Table 3 below, the mean scores in the cancer group of ADHC subjects (n=108) were significantly higher than in the cancer group of UDH subjects (n=111) (UDHC) (p value is 0.00484). These results demonstrate that the ADHC group can be differentiated from the UDHC group, which is often times difficult based on the morphological/histological assessment. Further, this differentiation was observed in the cohort of women who went on to develop breast cancer after 5 years or higher, but not in the control group.

TABLE 3

The Mean Risk Scores in the ADH and UDH types of cancer groups.

| Histology | Mean Score |
|---|---|
| ADHC | 7.600200 |
| UDHC | 4.927675 |

Example 10

Figure 15:
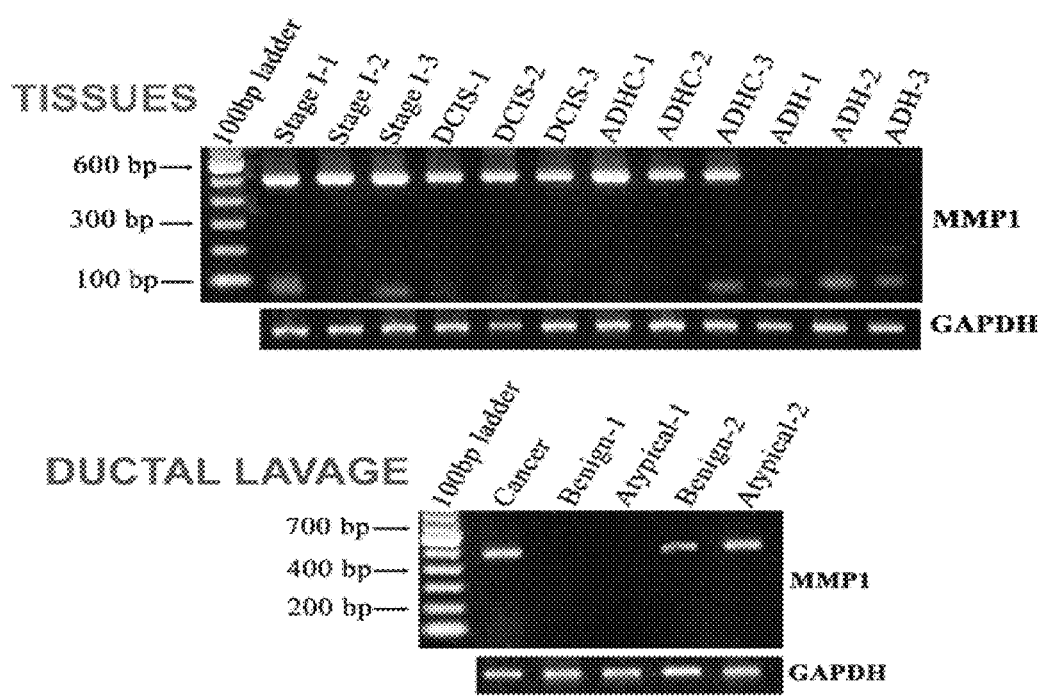
FIG. 15 includes representative images of MMP-1 mRNA levels measured by RT-PCR in stage 1 breast cancer tissues, DCIS cancer tissues, and atypical tissues from subjects who subsequently developed cancer (ADH), atypical tissues from subjects who did not develop cancer in at least five years (upper panel), and Ductal lavage samples (lower panel).

As shown in FIG. 15, expression of one of the risk prediction oncogenic markers, MMP-1, is shown, as measured by mRNA levels using RT-PCR in cancer tissues and atypical tissues from subjects who developed cancer (ADHC) (upper panel) and ductal lavage (DL) samples (lower panel). MMP-1 and GAPDH transcripts were amplified by PCR using cDNA prepared by reverse transcription of Ductal lavage cell total RNA or ADHC tissue total RNA. The PCR products were separated by 1% agarose gel electrophoresis and detected by ethidium bromide staining.

Example 11

Figure 16:
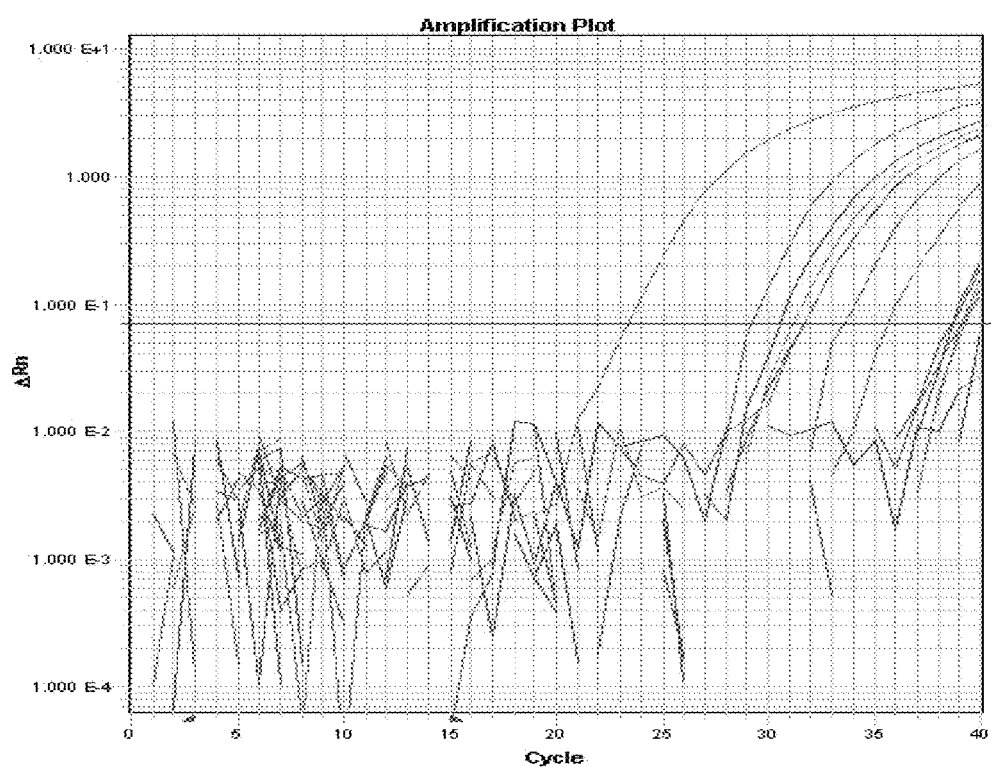
FIG. 16 is a representative amplification plot from RT-QPCR analysis of one of the oncogenic markers, CEACAM6, in breast ductal cells isolated from Ductal Lavage (DL).

Expression levels of CEACAM6 mRNA from cells isolated from ductal lavage (DL) samples by quantitative RT-PCR is shown in FIG. 16. As positive controls, breast cancer tumor tissue cDNA was used. Amplification was performed on samples which showed positive expression of the house keeping gene, GAPDH. A representative amplification plot is shown in FIG. 16, and Table 4 (below) shows examples of Ct values for 27 DL samples and two cancer tissue samples (M75 and M9).

TABLE 4

| Well | Sample Name | Detector Name | Ct |
|---|---|---|---|
| 33 | M75 | FAM | 29.349281 |
| 34 | M9 | FAM | 23.403864 |
| 37 | DL1 | FAM | Undetermined |
| 38 | DL-2 | FAM | Undetermined |
| 39 | DL-3 | FAM | Undetermined |
| 40 | DL-6 | FAM | Undetermined |
| 41 | DL-19 | FAM | 38.576553 |
| 42 | DL-27 | FAM | 31.697962 |
| 43 | DL-31 | FAM | Undetermined |
| 44 | DL-34 | FAM | Undetermined |
| 45 | DL-35 | FAM | 35.63518 |
| 46 | DL-36 | FAM | Undetermined |
| 49 | DL-37 | FAM | Undetermined |
| 50 | DL-38 | FAM | Undetermined |
| 51 | DL-39 | FAM | Undetermined |
| 52 | DL-40 | FAM | Undetermined |
| 53 | DL-42 | FAM | Undetermined |

TABLE 4-continued

| Well | Sample Name | Detector Name | Ct |
|---|---|---|---|
| 54 | DL-45 | FAM | 39.09891 |
| 55 | DL-51 | FAM | Undetermined |
| 56 | DL-54 | FAM | 39.18647 |
| 57 | DL-55 | FAM | Undetermined |
| 58 | DL-56 | FAM | 31.189604 |
| 61 | DL-58 | FAM | Undetermined |
| 62 | DL-59 | FAM | Undetermined |
| 63 | DL-60 | FAM | 30.478052 |
| 64 | DL-62 | FAM | Undetermined |
| 65 | DL-63 | FAM | 38.57952 |
| 66 | DL-64 | FAM | 31.708744 |
| 67 | DL-65 | FAM | 33.633224 |
| 68 | DL-66 | FAM | 39.08131 |

Example 12

In Table 5 below, Ductal Lavage samples were tested in subjects who had no detectable tumor tissue by mammography for positive mRNA expression using quantitative RT-PCR of two of the four oncogenic markers MMP-1 and CEACAM6. Marker expression in two DL samples from cancer patients are also shown as positive controls.

TABLE 5

| | | # Samples Positive for: | |
|---|---|---|---|
| Cytology Diagnosis | # Samples Tested | MMP-1 | CEACAM6 |
| Cancer | 2 | 2 | 2 |
| Atypia | 12 | 7 | 6 |
| Benign | 28 | 4 | 3 |
| Total | 42 | 13 | 11 |

Example 13

As shown in FIG. 17A-17B, mRNA expression levels of CEACAM6 (FIG. 17A) and MMP-1 (FIG. 17B) were measured by quantitative RT-PCR in DCIS tumors (orange bars), invasive breast cancer (IBC) tumors (red bars), and ductal lavage (DL; DL cells from cancer patients (black/red bars); atypical DL cells (pink bars); and benign DL cells (green bars)); samples were normalized to the house keeping gene, GAPDH.

6. MATERIALS AND METHODS

Control precancerous tissues, which include ADH, ALH, UDH, ULH and PAP, were obtained from subjects who had no prior breast cancer and did not develop for 5 or more years. The test case precancerous tissue (also referred to as "case" or "test case"), which includes ADHC, ALHC, UDHC and PAPH, were obtained from subjects who subsequently developed cancer after a minimum of 1 year and up to 5 or more years. These tissues were obtained from patients who subsequently developed ER+ and ER− cancers, independent of PR, Her2, nodal status, stage, grade, or histology of the cancer developed. All the test cases and controls in the study were obtained from subjects who had not received any preventive treatments. In both test cases and controls, atypical and non-atypical (e.g., papillomas, UDH and Sclerosing adenosis) types of tissues were included. For the atypical category, both atypical ductal and atypical lobular hyperplasias were included. All samples were obtained from UCLA medical school pathology division and Leeds hospitals Pathology division.

Specimens were retrieved without a subject's identifying information in the following steps: 1) identified specimens with follow up information; 2) retrieved all the H & E slides for each specimen; 3) identified which block had the desired tissue; 4) retrieved blocks; 5) cut 5-8 micron sections; and 6) the first and last cut sections from a block were examined after H &E staining to ascertain the sections in between have the intact histology. A minimum 5 year clinical follow up was chosen because the mean time period between proliferative diagnosis and cancer development in test cases was about 3 years.

To understand the biology of the precancerous tissues from subjects that subsequently developed cancer, the top 200 differentially expressed genes in ADHC were analyzed to map the disrupted pathways using IPA program. For Immunohistochemical (IHC) detection of markers, unstained paraffin-embedded tumor tissue sections were immuno-stained using specific antibodies. Briefly, slides were deparaffinized in 2 changes of xylene and gradually re-hydrated by passing through graded EtOH. Antigens were unmasked by treating the slides in a steamer and staining was performed using specific antibodies. The slides were washed and incubated with peroxidase substrate. Finally, the slides were washed and stained with Haematoxylin, mounted. All IHC stained slides were evaluated by a pathologist and the staining intensities were graded from 0.5 to 4.0.

Expression data of several cancer markers were statistically analyzed to determine Sensitivity, Specificity, Positive Predictive Value (PPV) (correctly predicting cancer development in women who were positive), and Negative Predictive Value (NPV) (correctly predicting non-development of cancer in women who were negative). The significance of marker expression and cancer development was evaluated using chi-square test. The Receiver Operating Characteristic (ROC) curves were drawn for various combinations of markers for predicting the risk of cancer development.

To generate "Risk Scores" based on expression level of multiple markers, the risk scores for each sample was calculated by logistic regression in the following steps: 1) IHC scores of each marker for all the samples were analyzed by logistic regression to obtain coefficients for each marker; and 2) Risk Scores of combinations of markers were obtained by first multiplying IHC grades of each marker with its respective regression coefficient for each sample and obtaining values, and subsequently adding the obtained values of all the markers in a sample to derive "Composite Risk Score" for the combination of markers.

To derive "Risk Prediction Probability Scores" (average risk scores) and % accuracy to predict risk, the distribution of risk scores (scaled from 0-10) of Controls and Test Cases were analyzed using scattered plots and density plots. From the risk score distribution plots, the estimates of scores that predict the probability of cancer development and 95% confidence Intervals were calculated. From the risk score distribution data of Controls and Test Cases, cancer predictability rate was determined with a margin of error and significant level.

The Risk Score Data were also analyzed for cancer free survival by Kaplan Meier curves to generate cancer free rates for risk stratification.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

Clause 1. A method of predicting cancer in a subject, the method comprising: quantifying levels of at least two oncogenic biomarkers or fragments thereof from a hyperplastic tissue sample from a subject; calculating a risk score based on the levels of the at least two oncogenic biomarkers or fragments thereof and determining that the subject has a low, intermediate or high risk of developing cancer based on the calculated risk score.

Clause 2. The method of clause 1, wherein one of the at least two oncogenic biomarkers is selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

Clause 3. The method of clause 1, wherein the at least two oncogenic biomarkers are selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

Clause 4. The method of any of clauses 1 to 3, wherein quantifying levels of the at least two oncogenic biomarkers or fragments thereof from the hyperplastic tissue sample from the subject comprises an assay having a sensitivity of at least 80% and a specificity of at least 70%.

Clause 5. The method of any of clauses 1 to 4, wherein quantifying levels of the at least two oncogenic biomarkers or fragments thereof from the hyperplastic tissue sample from the subject comprises an assay having a negative predictive value (NPV) of at least 90% and a positive predictive value (PPV) of at least 70%.

Clause 6. The method of clause 1, wherein the method comprises quantifying the levels of at least three oncogenic biomarkers selected from the group consisting of HEC1, CEACAM6, HYAL1, and MMP-1.

Clause 7. The method of clause 6, wherein quantifying levels of the at least three oncogenic biomarkers or fragments thereof from the hyperplastic tissue sample from the subject comprises an assay having a sensitivity of at least 80% and a specificity of at least 70%.

Clause 8. The method of clause 6, wherein quantifying levels of the at least three oncogenic biomarkers or fragments thereof from the hyperplastic tissue sample from the subject comprises an assay having a negative predictive value (NPV) of at least 80% and a positive predictive value (PPV) of at least 80%.

Clause 9. The method of clause 1, wherein the method comprises quantifying the levels of at least four oncogenic biomarkers selected from the group consisting of HEC1, CEACAM6, HYAL1, and MMP-1.

Clause 10. The method of clause 9, wherein quantifying levels of the at least four oncogenic biomarkers or fragments thereof from the hyperplastic tissue sample from the subject comprises an assay having a sensitivity of at least 80% and a specificity of at least 80%.

Clause 11. The method of clause 9, wherein quantifying levels of the at least four oncogenic biomarkers or fragments thereof from the hyperplastic tissue sample from the subject comprises an assay having a negative predictive value (NPV) of at least 80% and a positive predictive value (PPV) of at least 80%.

Clause 12. The method of any of clauses 1 to 11, wherein quantifying the levels of the at least two oncogenic biomarkers comprises one or more of Western blot analysis, a protein/peptide function assay, immunohistochemistry analysis, ELISA analysis, DNA chip analysis, or mRNA analysis by one or more of reverse transcription-polymerase chain reaction (RT-PCR), competitive RT-PCR, real-time RT-PCR, digital PCR, RNase protection assay (RPA), Next Generation RNA sequencing, microarray analysis, and Northern blotting.

Clause 13. The method of any of clauses 1 to 12, wherein a risk score equal to or less than 1 indicates a low risk of the subject developing cancer, a risk score greater than 1 but equal to or less than 5 indicates an intermediate risk of the subject developing cancer, and a risk score of greater than 5 indicates a high risk of the subject developing cancer.

Clause 14. The method of clause 13, wherein: i) a risk score categorized as low indicates that the subject has a cancer free survival rate of at least 95% for at least 19 years; ii) a risk score categorized as intermediate indicates that the subject has a cancer free survival rate of at least 95% for at least 5 years and a cancer free survival rate of least 75% for at least 10 years; and iii) a risk score categorized as high indicates that the subject has a cancer free survival rate of at most 45% for at least 5 years and a cancer free survival rate of at least 20% for at least 10 years.

Clause 15. The method of any of clauses 1 to 14, wherein the hyperplastic tissue sample is obtained using at least one of a core biopsy, a surgical biopsy, a fine needle aspiration procedure, ductal lavage, a nipple aspirate fluid procedure, and nipple discharge collection.

Clause 16. The method of any of clauses 1 to 15, wherein the hyperplastic tissue sample is obtained from at least one of breast tissue, ovarian tissue, blood, urinary track tissue, kidney tissue, lymphatic tissue, brain tissue, bone tissue, genital tract tissue, gastrointestinal tract tissue, nervous system tissue, prostate tissue, testicular tissue, lung tissue, head and neck tissue, and immune system tissue.

Clause 17. The method of any of clauses 1 to 16, wherein the subject is a human mammal without a history of cancer.

Clause 18. The method of any of clauses 1 to 17, further comprising treating the subject with a therapeutic anti-cancer agent.

Clause 19. The method of clause 18, wherein the therapeutic agent comprises at least one of tamoxifen, raloxifen, and an aromatase inhibitor.

Clause 20. The method of any of clauses 1 to 19, further comprising treating the subject using a surgical therapy.

Clause 21. The method of clause 20, wherein the surgical therapy is mastectomy.

Clause 22. A biomarker panel for determining cancer risk in a subject, the panel comprising at least two of the following oncogenic biomarkers: HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1); wherein quantification of levels of the at least two oncogenic biomarkers or fragments thereof is used to calculate a risk score predictive of a low, intermediate, or high risk of developing cancer.

Clause 23. The biomarker panel of clause 22, wherein the panel comprises at least three of the following biomarkers: HEC1, CEACAM6, HYAL1, and MMP-1.

Clause 24. The biomarker panel of clause 22, wherein the panel comprises at least the four following biomarkers: HEC1, CEACAM6, HYAL1, and MMP-1.

Clause 25. The biomarker panel of any of clauses 22 to 24, wherein a risk score equal to or less than 1 indicates a low risk of the subject developing cancer, a risk score greater than 1 but equal to or less than 5 indicates an intermediate risk of the subject developing cancer, and a risk score of greater than 5 indicates a high risk of the subject developing cancer.

Clause 26. A method of classifying a patient who may be at risk of developing cancer, the method comprising: quantifying levels of at least two oncogenic biomarkers or fragments thereof from a hyperplastic tissue sample from a subject; calculating a risk score based on the levels of the at least two oncogenic biomarkers or fragments thereof; and classifying the subject as having a low, intermediate or high risk of developing cancer based on the calculated risk score.

Clause 27. The method of clause 26, wherein one of the at least two oncogenic biomarkers is selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

Clause 28. The method of clause 26, wherein the at least two oncogenic biomarkers are selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

Clause 29. The method of clause 26, wherein the method comprises quantifying the levels of at least three oncogenic biomarkers selected from the group consisting of HEC1, CEACAM6, HYAL1, and MMP-1.

Clause 30. The method of clause 26, wherein the method comprises quantifying the levels of at least four oncogenic biomarkers selected from the group consisting of HEC1, CEACAM6, HYAL1, and MMP-1.

Clause 31. The method of any of clauses 26 to 30, wherein a risk score equal to or less than 1 indicates a low risk of the subject developing cancer, a risk score greater than 1 but equal to or less than 5 indicates an intermediate risk of the subject developing cancer, and a risk score of greater than 5 indicates a high risk of the subject developing cancer.

Clause 32. A method of monitoring a patient at risk for cancer, the method comprising: quantifying levels of at least two oncogenic biomarkers or fragments thereof from a first hyperplastic tissue sample from a subject; calculating a first risk score based on the levels of the at least two oncogenic biomarkers or fragments thereof from the first hyperplastic tissue sample; determining that the subject has a low, intermediate or high risk of developing cancer based on the calculated risk score; administering to the subject having an intermediate or high risk of developing cancer an anti-cancer agent for a period of time to prevent cancer; obtaining a second hyperplastic or non-hyperplastic tissue sample from the subject; evaluating the change in the levels of the at least two oncogenic biomarkers or fragments thereof from the second hyperplastic or non-hyperplastic tissue sample based on the first hyperplastic tissue sample; calculating a second risk score based on the levels of the at least two oncogenic biomarkers or fragments thereof; and comparing the first risk score with the second risk score and determining whether to (i) discontinue use of the anti-cancer agent in the subject; (ii) continue treatment with the anti-cancer agent in the subject; or (iii) administer a different anti-cancer agent to the subject based on the comparison of the first and second risk scores.

Clause 33. The method of clause 32, wherein treatment with the anti-cancer agent is discontinued because the second risk score is lower than the first risk score.

Clause 34. The method of clause 32, wherein the treatment with the anti-cancer agent is continued because the first and second risk scores are identical.

Clause 35. The method of clause 32, wherein the treatment with the anti-cancer agent is discontinued and treatment with a new anti-cancer agent is administered to the patient because the second risk score is higher than the first risk score.

Clause 36. A method of monitoring a subject at risk cancer, the method comprising: obtaining a surgically removed precancerous hyperplastic or non-hyperplastic tissue sample from a subject; quantifying levels of at least two oncogenic biomarkers or fragments thereof from the sample; calculating a risk score based on the levels of the at least two oncogenic biomarkers or fragments thereof; determining that the subject has a low, intermediate or high risk of developing cancer based on the calculated risk score; and administering to the subject having an intermediate or high risk of developing cancer an anti-cancer agent to prevent the cancer from developing.

What is claimed is:

1. A method of predicting breast cancer in a subject, the method comprising:
    quantifying levels of at least two oncogenic biomarkers or fragments thereof from a hyperplastic tissue sample from a subject, wherein the at least two oncogenic biomarkers comprise HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1);
    calculating a risk score based on the levels of the at least two oncogenic biomarkers or fragments thereof, wherein a risk score equal to or less than 1 indicates that the subject has a cancer free survival rate of at least 95% for at least 19 years, a risk score greater than 1 but equal to or less than 5 indicates that the subject has a cancer free survival rate of at most 95% for at least 5 years and at least 75% for at least 10 years, and a risk score of greater than 5 indicates that the subject has a cancer free survival rate of at most 45% for at least 5 years and at least 20% for at least 10 years; and
    treating the subject having a risk score of greater than 5 with an effective amount of an anti-cancer agent.

2. The method of claim 1, wherein one of the at least two oncogenic biomarkers is HEC1.

3. The method of claim 1, wherein the at least two oncogenic biomarkers are selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

4. The method of claim 1, wherein quantifying levels of the at least two oncogenic biomarkers or fragments thereof from the hyperplastic tissue sample from the subject comprises an assay having a sensitivity of at least 80% and a specificity of at least 70%.

5. The method of claim 1, wherein quantifying levels of the at least two oncogenic biomarkers or fragments thereof from the hyperplastic tissue sample from the subject comprises an assay having a negative predictive value (NPV) of at least 90% and a positive predictive value (PPV) of at least 70%.

6. The method of claim 1, wherein the method comprises quantifying the levels of at least three oncogenic biomarkers selected from the group consisting of HEC1, CEACAM6, HYAL1, and MMP-1.

7. The method of claim 6, wherein quantifying levels of the at least three oncogenic biomarkers or fragments thereof from the hyperplastic tissue sample from the subject comprises an assay having a sensitivity of at least 80% and a specificity of at least 70%.

8. The method of claim 6, wherein quantifying levels of the at least three oncogenic biomarkers or fragments thereof from the hyperplastic tissue sample from the subject comprises an assay having a negative predictive value (NPV) of at least 80% and a positive predictive value (PPV) of at least 80%.

9. The method of claim 1, wherein the method comprises quantifying the levels of at least four oncogenic biomarkers selected from the group consisting of HEC1, CEACAM6, HYAL1, and MMP-1.

10. The method of claim 9, wherein quantifying levels of the at least four oncogenic biomarkers or fragments thereof from the hyperplastic tissue sample from the subject comprises an assay having a sensitivity of at least 80% and a specificity of at least 80%.

11. The method of claim 9, wherein quantifying levels of the at least four oncogenic biomarkers or fragments thereof from the hyperplastic tissue sample from the subject comprises an assay having a negative predictive value (NPV) of at least 80% and a positive predictive value (PPV) of at least 80%.

12. The method of claim 1, wherein quantifying the levels of the at least two oncogenic biomarkers comprises one or more of Western blot analysis, a protein/peptide function assay, immunohistochemistry analysis, ELISA analysis, DNA chip analysis, or mRNA analysis by one or more of reverse transcription-polymerase chain reaction (RT-PCR), competitive RT-PCR, real-time RT-PCR, digital PCR, RNase protection assay (RPA), Next Generation RNA sequencing, and Northern blotting.

13. The method of claim 1, wherein the hyperplastic tissue sample is obtained using at least one of a core biopsy, a surgical biopsy, a fine needle aspiration procedure, ductal lavage, a nipple aspirate fluid procedure, and nipple discharge collection.

14. The method of claim 1, wherein the subject is a human mammal without a history of breast cancer.

15. The method of claim 1, wherein the anti-cancer agent comprises at least one of tamoxifen, raloxifen, and an aromatase inhibitor.

16. The method of claim 1, further comprising treating the subject using a surgical therapy.

17. The method of claim 16, wherein the surgical therapy is mastectomy.

18. A method of classifying a patient who may be at risk of developing breast cancer, the method comprising:

quantifying levels of at least two oncogenic biomarkers or fragments thereof from a hyperplastic tissue sample from a subject, wherein the at least two oncogenic biomarkers comprise HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1);

calculating a risk score based on the levels of the at least two oncogenic biomarkers or fragments thereof, wherein a risk score equal to or less than 1 indicates a low risk of the subject developing cancer, a risk score greater than 1 but equal to or less than 5 indicates an intermediate risk of the subject developing cancer, and a risk score of greater than 5 indicates a high risk of the subject developing cancer; and classifying the subject as having a low, intermediate or high risk of developing cancer based on the calculated risk score, wherein a low risk indicates that the subject has a cancer free survival rate of at least 95% for at least 19 years, an intermediate risk indicates that the subject has a cancer free survival rate of at most 95% for at least 5 years and at least 75% for at least 10 years, and a high risk indicates that the subject has a cancer free survival rate of at most 45% for at least 5 years and at least 20% for at least 10 years.

19. The method of claim 18, wherein one of the at least two oncogenic biomarkers is HEC1.

20. The method of claim 18, wherein the at least two oncogenic biomarkers are selected from the group consisting of HEC1 (Highly Expressed in Cancer protein), CEACAM6 (Carcino Embryonic Antigen Cell Adhesion Molecule 6), HYAL1 (Hyaluronoglucosaminidase 1), and MMP-1 (Matrix Metalloproteinase-1).

21. The method of claim 18, wherein the method comprises quantifying the levels of at least three oncogenic biomarkers selected from the group consisting of HEC1, CEACAM6, HYAL1, and MMP-1.

22. The method of claim 18, wherein the method comprises quantifying the levels of at least four oncogenic biomarkers selected from the group consisting of HEC1, CEACAM6, HYAL1, and MMP-1.

* * * * *